US010512888B2

(12) United States Patent
Pighin et al.

(10) Patent No.: US 10,512,888 B2
(45) Date of Patent: Dec. 24, 2019

(54) MULTIPLE IDENTIFICATION POINT AUTOMATED PARAMETER ASSURANCE METHOD

(71) Applicant: Parker-Hannifin Corporation, Cleveland, OH (US)

(72) Inventors: Dean James Pighin, Stoughton, WI (US); Richard Krmit Bergs, Madison, WI (US); Donald Robert Beers, Madison, WI (US); Peter Anthony D'Antonio, Jr., Marlton, NJ (US)

(73) Assignee: Parker-Hannifin Corporation, Cleveland, OH (US)

( * ) Notice: Subject to any disclaimer, the term of this patent is extended or adjusted under 35 U.S.C. 154(b) by 476 days.

(21) Appl. No.: 15/319,683

(22) PCT Filed: Jun. 23, 2015

(86) PCT No.: PCT/US2015/037103
§ 371 (c)(1),
(2) Date: Dec. 16, 2016

(87) PCT Pub. No.: WO2015/200269
PCT Pub. Date: Dec. 30, 2015

(65) Prior Publication Data
US 2017/0128905 A1   May 11, 2017

Related U.S. Application Data

(60) Provisional application No. 62/016,476, filed on Jun. 24, 2014.

(51) Int. Cl.
*B01D 61/20* (2006.01)
*B01D 61/22* (2006.01)
(Continued)

(52) U.S. Cl.
CPC ............. *B01J 19/004* (2013.01); *B01D 61/20* (2013.01); *B01D 61/22* (2013.01);
(Continued)

(58) Field of Classification Search
CPC ........ B01D 15/10; B01D 15/14; B01D 17/12; B01D 61/10; B01D 61/12; B01D 61/20;
(Continued)

(56) References Cited

U.S. PATENT DOCUMENTS 3,775,595 A * 11/1973 Rosse ............... G01N 35/00594
219/432
3,796,239 A * 3/1974 Zindler .................. G01N 35/00
141/192

(Continued)

FOREIGN PATENT DOCUMENTS

CN        1062299       7/1992
CN        1928565       3/2007
(Continued)

OTHER PUBLICATIONS

International Search Report and the Written Opinion of the International Searching Authority of PCT/US2015/037,103, dated Oct. 7, 2015.
(Continued)

*Primary Examiner* — Joseph W Drodge
(74) *Attorney, Agent, or Firm* — Cook Alex Ltd.

(57) ABSTRACT

Systems and methods provide automated parameter assurance features and results for consumables used in bioprocessing and particularly for purifying, filtering, harvesting and collecting bioprocessing fluids. Consumables having these features are sized, shaped, configured and constructed to interface with and be a component of such a bioprocessing system that includes a multi-use component or device with which it operatively engages such as by docking, engage-
(Continued)

ment with a connector or other approach that allows for insertion and removal of the consumable. The consumable may be a component having a single-use life or a limited life. Each consumable has a median by which information, which can include use limits and specifications, is associated with that specific consumable, and those limits and specifications are communicated to the multi-use component which indicates any inappropriateness for use with the multi-use component.

16 Claims, 21 Drawing Sheets

(51) Int. Cl.
  *B01J 19/00* (2006.01)
  *C12M 1/00* (2006.01)
  *C12M 1/36* (2006.01)

(52) U.S. Cl.
  CPC ....... *B01D 2313/125* (2013.01); *C12M 23/40* (2013.01); *C12M 29/00* (2013.01); *C12M 41/48* (2013.01)

(58) Field of Classification Search
  CPC ........ B01D 61/22; B01D 61/30; B01D 61/32; B01D 2311/24; B01D 2311/26; B01D 2313/105; B01D 2313/125; B01J 19/0006; B01J 19/004; B01J 2219/00049; B01J 2219/00225; B01J 2219/0054; B01J 2219/00547; B01J 2219/00554; C12M 23/00; C12M 23/40; C12M 29/00; C12M 29/04; C12M 41/48; C12M 45/04; C12M 45/22; C12M 47/12; G01N 1/34; G01N 1/40; G01N 1/4005; G01N 2001/4016; G01N 2001/4088; G01N 30/02; G01N 30/06; G01N 30/20; G01N 30/24; G01N 30/38; G01N 2030/201
  USPC ..... 210/85, 91, 143, 198.2, 321.6, 650, 656, 210/739; 221/2; 222/22, 53; 235/435; 422/105, 129; 435/261, 286.1, 286.2, 435/286.4, 289.1, 308.1
  See application file for complete search history.

(56) References Cited

U.S. PATENT DOCUMENTS

| | | | |
|---|---|---|---|
| 6,564,655 B1* | 5/2003 | Austen | G01N 1/14 73/863.01 |
| 2003/0153844 A1* | 8/2003 | Smith | A61B 10/0051 600/573 |
| 2003/0230521 A1* | 12/2003 | Schick | A61M 1/0209 210/110 |
| 2006/0027500 A1* | 2/2006 | Schick | B01D 15/14 210/650 |
| 2006/0118472 A1* | 6/2006 | Schick | B01D 61/18 210/198.2 |
| 2007/0255527 A1* | 11/2007 | Schick | A61M 1/3621 702/179 |
| 2008/0230607 A1* | 9/2008 | Etten | G06K 7/10 235/435 |
| 2008/0233653 A1 | 9/2008 | Hess et al. | |
| 2009/0180513 A1* | 7/2009 | Schick | A61M 1/3621 374/44 |
| 2009/0277824 A1* | 11/2009 | Giglia | A61L 2/0017 210/321.6 |
| 2010/0219238 A1* | 9/2010 | Mallett | B07C 5/3412 235/375 |
| 2011/0097245 A1 | 4/2011 | Elizarov et al. | |
| 2012/0074214 A1 | 3/2012 | Mizumoto et al. | |
| 2012/0242993 A1* | 9/2012 | Schick | G01N 21/0303 356/442 |
| 2012/0325902 A1* | 12/2012 | Goyal | G06F 17/00 235/375 |
| 2013/0020727 A1 | 1/2013 | Klausing et al. | |
| 2014/0011295 A1 | 1/2014 | Ammann et al. | |
| 2014/0170758 A1 | 6/2014 | Bailer et al. | |
| 2014/0229152 A1 | 8/2014 | Chisholm | |
| 2014/0263674 A1* | 9/2014 | Cerveny | G06K 19/06028 235/494 |

FOREIGN PATENT DOCUMENTS

| | | |
|---|---|---|
| CN | 102539797 A | 7/2012 |
| WO | WO 2013/049608 A2 | 4/2013 |

OTHER PUBLICATIONS

Australian IP Office Examination Report in AU 2015280223 dated Jul. 26, 2018.
State IP Office of China, First Search Report, in translation dated Aug. 7, 2018.
State IP Office of China, Second Search Report, in translation dated Feb. 28, 2019.

* cited by examiner

FIG. 7

METHOD MAINTENANCE

[FLUSH] [FILTRATION] [INTEGRITY LOST]   [PURGE]

[▽]   [LOAD RECIPE]

RECIPE:

NAME (HOME) (ALARMS)   [BACK]

FIG. 8

FLUSH METHOD

MAX FLUSH TIME: [0.0] MINUTES
FLUSH RATE: [00.0] LPM
MAX FLUSH PRESSURE: [00.0] BAR
FLUSH BAG: [V2-4 WASTE FLUSH BAG ▽]

SAVE AS RECIPE: [      ]  [SAVE]

(HOME) (ALARMS)   [BACK]

FIG. 9

INTEGRIT TEST

TEST DURATION: [0.0] MINUTES
FILTER CONTENTS: [     ]
MAX PRESSURE: [00.0] BAR
PURGE BAG: [V2-4 WASTE FLUSH BAG ▽]

SAVE AS RECIPE: [      ]  [SAVE]

(HOME) (ALARMS)   [BACK]

FIG. 19

ALARMS MANAGEMENT

MAX PRESSURE P1 [2.07BAR] [0.00BAR] [SET]
MIN PRESSURE P1 [0.07BAR] [0.00BAR] [SET]
MAX PRESSURE P2 [0.85BAR] [0.00BAR] [SET]
ON SYSTEM SCALE MAX WEIGHT: [50.000] [0.000] [SET]
ON SYSTEM SCALE MIN WEIGHT: [0.000] [0.000] [SET]

OFF SYSTEM SCALE MAX WEIGHT [50.00] [0.00]KG [SET]
OFF SYSTEM SCALE MIN WEIGHT [0.00] [0.00]KG [SET]
OFF SYSTEM SCALE STATE [OFF ▽]

(HOME) (ALARMS) [BACK]

FIG. 20

CONSTANTS [RESTORE DEFAULTS]
MAX SCALE WEIGHT SETPOINT (51 OR 52) [0.00] KG
MIN SCALE WEIGHT SETPOINT (51 OR 52) [0.00] KG
MAX FLOW WM 620 17 MM [13.00] L/MIN
MIN FLOW WM 620 17 MM [0.65] L/MIN
MAX FLOW WM 620 12 MM [0.60] L/MIN
MIN FLOW WM 620 12 MM [0.42] L/MIN
MAX RECIPE PRESSURE (P1 & P2) [0.00] BAR
MIN RECIPE PRESSURE (P1 ONLY) [0.00] BAR
NUMBER OF LABELS TO PRINT [0]

MAX FLOW WM 520 9.6 MM [3.500] L/MIN
MIN FLOW WM 520 9.6 MM [3.500] L/MIN
MAX FLOW WM 520 8.0 MM [2.400] L/MIN
MIN FLOW WM 520 8.0 MM [2.400] L/MIN
MAX FLOW WM 520 6.4 MM [1.500] L/MIN
MIN FLOW WM 520 6.4 MM [1.500] L/MIN
MAX FLOW WM 520 4.0 MM [0.870] L/MIN
MIN FLOW WM 520 4.0 MM [0.870] L/MIN
MAX FLOW WM 520 3.2 MM [0.390] L/MIN
MIN FLOW WM 520 3.2 MM [0.390] L/MIN
AUX ANALOG SCALE SPAN [0.00] KG (HOME) (ALARMS)

FIG. 21

TRENDING

A1 A2 A3 A4    14:42:00  14:46:00  14:50:00  14:54:00  14:58:00
                              TIME (HOME) (ALARMS)  PRESSURE P1(BAR)-A4    PUMP U1 FLOW(LPM)-A2
                 PRESSURE P2(BAR)-A4    PUMP U2 FLOW(LPM)-A2
                 SCALE 51(KG)-A3        AIR FLOW(SCCM)-A1
                 SCALE 52(KG)-A3

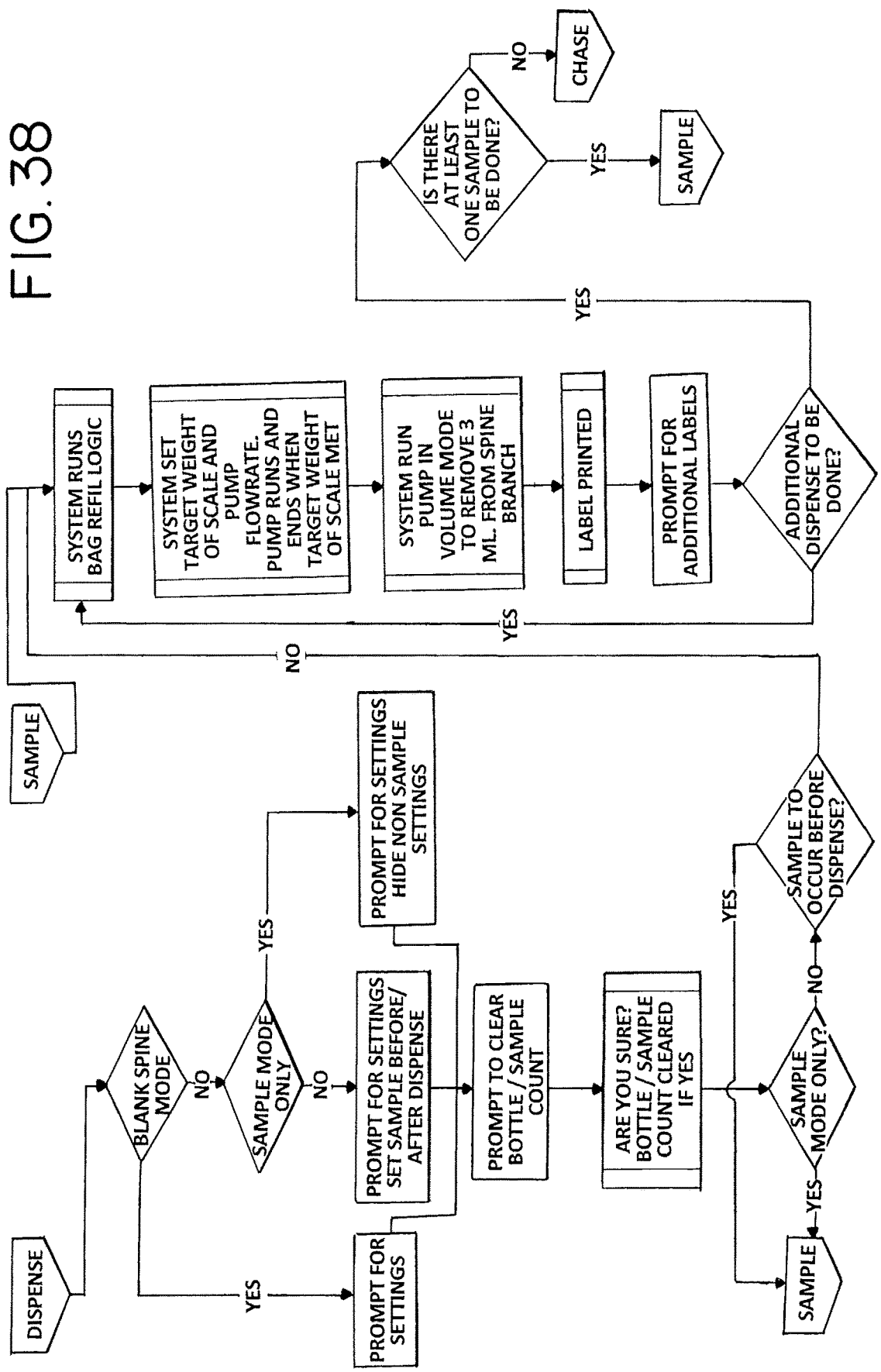

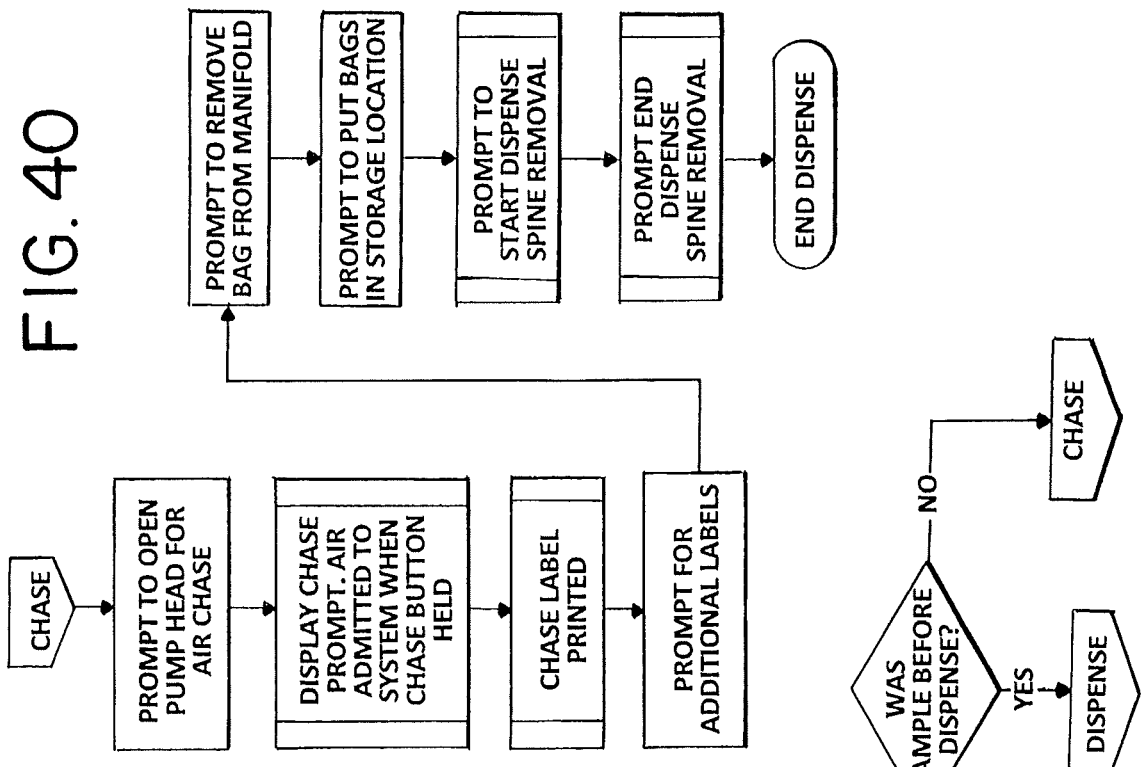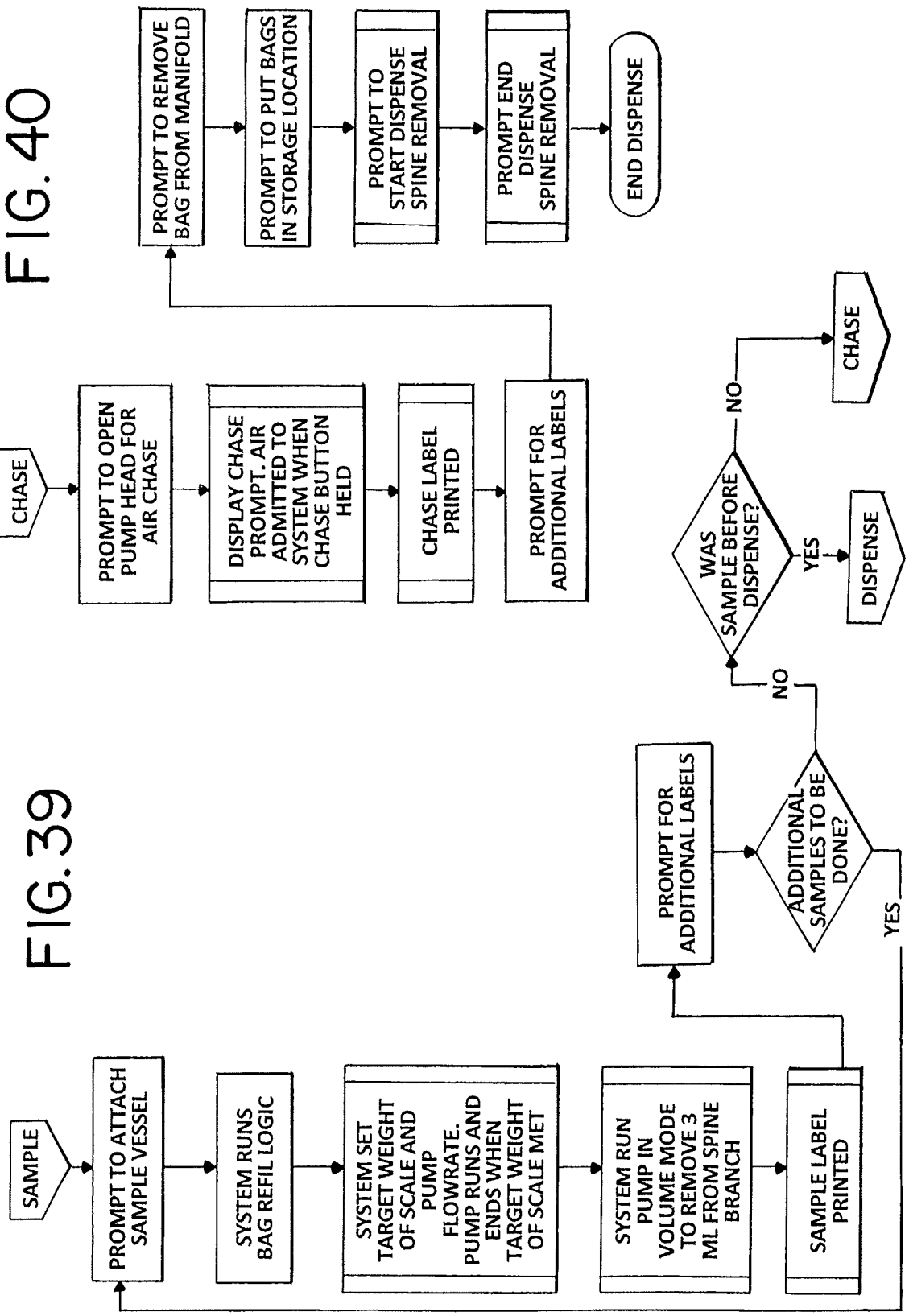

MULTIPLE IDENTIFICATION POINT AUTOMATED PARAMETER ASSURANCE METHOD

CROSS REFERENCE STATEMENT

This application is a National Phase of PCT/US2015/037,103, filed Jun. 23, 2015, which claims priority from U.S. Patent Application Ser. No. 62/016,476, filed Jun. 24, 2014, and the entire disclosure of each is hereby incorporated by reference.

FIELD OF THE DISCLOSURE

The present subject matter generally relates to systems such as manifold systems for biopharmaceutical fluids processing that incorporate consumables having at least one tolerance specification related to the system.

BACKGROUND

Biopharmaceutical manufacturing and clinical production facilities are known to employ single-use components or consumables that are provided in ready-to-use condition such as exhibiting adequate sterilization required for intended uses. Consumables also are employed in processing and purification of bioreactor solutions, including unit-operational platforms for aseptic purification and/or processing of solutions by normal flow filtration ("NFF"), tangential flow filtration ("TFF"), chromatography, preparative chromatography, bioreactor applications, and so forth.

Methods and systems in this regard have been known to include a combination of reusable or multi-use non-consumable components along with single-use, disposable or consumable components, often in the context of manifold systems and/or modular systems assembled or modified according to the intended use, such as NFF, TFF and so forth. Systems and methods of these types of manifolds, modular arrangements and single-use components are noted in U.S. Pat. Nos. 6,712,963, 7,052,603, 7,410,587, 6,350,382, 6,607,669, 7,857,506, 7,788,047, 7,927,010, 8,506,162, and 8,817,259, and U.S. Published Patent Applications No. 2006/0118472, No. 2013/0131245, No. 2014/0060161 and No. 2014/0353516, each incorporated in its entirety hereinto by reference. Methods and systems of this general type include disposable or consumable components such as tubing, valves, connectors, pinch valves, sensors, bags, bioreactor bags, flow-through analysis tubes, containers, and collection bags.

SUMMARY

The present disclosure concerns systems and methods having automated parameter assurance features, typically exhibiting multiple identification point features. Such parameter assurance capabilities are particularly directed to components for these types of systems that are of the consumable, single-use or disposable types. Generally, operating logic interrogates for and detects compliance or lack of compliance with desired parameters. Typically, the operating logic detects operation inconsistent with the readable tolerance specification and indicates non-suitability for use in the system or method.

One embodiment concerns manifold systems and methods for biopharmaceutical fluids processing, the system including consumables and non-consumables, each having a predetermined function, wherein the consumables and non-consumables combine into a system for biopharmaceutical fluids processing of a selected type or types. At least one consumable of the system has a specific consumable characteristic readable tolerance specification that defines suitability of the consumable for use in the manifold system, while the non-consumable includes operating logic that controls interrogation of the specific consumable with respect to its specific readable tolerance specification.

Another embodiment concerns systems and methods for biopharmaceutical fluids processing, the system including consumables and non-consumables, each having a predetermined function, wherein the consumables and non-consumables combine into a system and method for biopharmaceutical fluids processing of a selected type or types. At least one consumable of the system or method has a specific consumable characteristic readable tolerance specification that defines suitability of the consumable for use in the system or method, while the non-consumable includes operating logic that controls interrogation of the specific consumable with respect to its specific readable tolerance specification that is an operational detail, a parameter specification, or a combination thereof.

A further embodiment concerns systems or methods for biopharmaceutical fluids processing, the system including consumables and non-consumables, each having a predetermined function, wherein the consumables and non-consumables combine into a system or method for biopharmaceutical fluids processing of a selected type or types. At least one consumable has a specific consumable characteristic readable tolerance specification that defines suitability of the consumable for use in the system or method, while the non-consumable includes operating logic that controls interrogation of the specific consumable with respect to its specific readable tolerance specification embedded within the specific consumable.

One embodiment concerns manifold systems or methods for biopharmaceutical fluids processing, the system including consumables and non-consumables, each having a predetermined function, wherein the consumables and non-consumables combine into a system for biopharmaceutical fluids processing of a selected type or types. At least one consumable has a specific consumable characteristic readable tolerance specification that defines suitability of the consumable for use in the manifold system or method, while the non-consumable includes operating logic that controls interrogation of the specific consumable with respect to its specific readable tolerance specification. The specific consumable is recognized as non-genuine for use in that manifold system when the readable tolerance specification is interrogated and determined to be inconsistent with the readable tolerance specification for that consumable.

A further embodiment concerns manifold systems and methods for biopharmaceutical fluids processing, the system including consumables and non-consumables, each having a predetermined function, wherein the consumables and non-consumables combine into a system or method for biopharmaceutical fluids processing of a selected type or types. At least one consumable has a specific consumable characteristic readable tolerance specification that defines suitability of the consumable for use in the manifold system, while the non-consumable includes operating logic that controls interrogation of the specific consumable with respect to its specific readable tolerance specification. In this embodiment, the readable tolerance specification is embedded with the specific consumable and includes a multipoint storage device for the embedded specific consumable.

In an embodiment, a parameter assurance and lock-out method is provided. An operator physically loads a consumable on the system, which captures consumable information such as a bar code scan, RFID memory key, wireless collection, etc., and checking ensues for genuine product and data validation for that specific consumable. If validation passes, the functions dependent on the consumable type are enabled. Validation failure is recognized and, when desired, prevents continued use.

In an embodiment, a parameter assurance and lock-out system or method is provided. An operator physically loads a consumable on the system, which captures consumable information such as a bar code scan, RFID memory key, wireless collection, etc., and checking ensues for genuine product and data validation for that specific consumable. If validation passes, the functions dependent on the consumable type are enabled. Validation failure is recognized and, when desired, prevents continued use. With functions enabled, and with operating limits, batch information, document storage requirements and/or automation sequence based on consumables are set, processing proceeds.

BRIEF DESCRIPTION OF THE DRAWINGS

FIG. 7 is a schematic maintenance method display where operators have the ability to modify or delete stored methods in the system, allowing parameter field population with stored values for that method, allowing for parameter modification as needed;

FIG. 8 is a schematic illustration of a flush method display and launching a parameter table and storage method screen where operators are able to create and store flush methods for the manifold;

FIG. 9 is a schematic illustration of integrity test display for launching a parameter table and storage method screen where operators are able to create and store filter integrity test methods;

FIG. 19 is a schematic illustration of an alarms management display allowing modification of alarm parameters;

FIG. 20 is a schematic illustration of a constants display allowing entry or modification of programmed constants tied to software;

FIG. 21 is a schematic illustration of a trending display for graphical representation of specific parameters;

FIG. 38 is a flow chart illustrating details of a filtration and dispense system dispense module to dispense product processed according to the system or method for collection thereof;

FIG. 39 is a flow chart illustrating details of a filtration and dispense system sample module for dispensing a sample portion of processed product; and FIG. 40 is a flow chart illustrating details of a filtration and dispense system chase module to clear processed product from the filling lines.

DESCRIPTION OF THE ILLUSTRATED EMBODIMENTS

Figure 1:
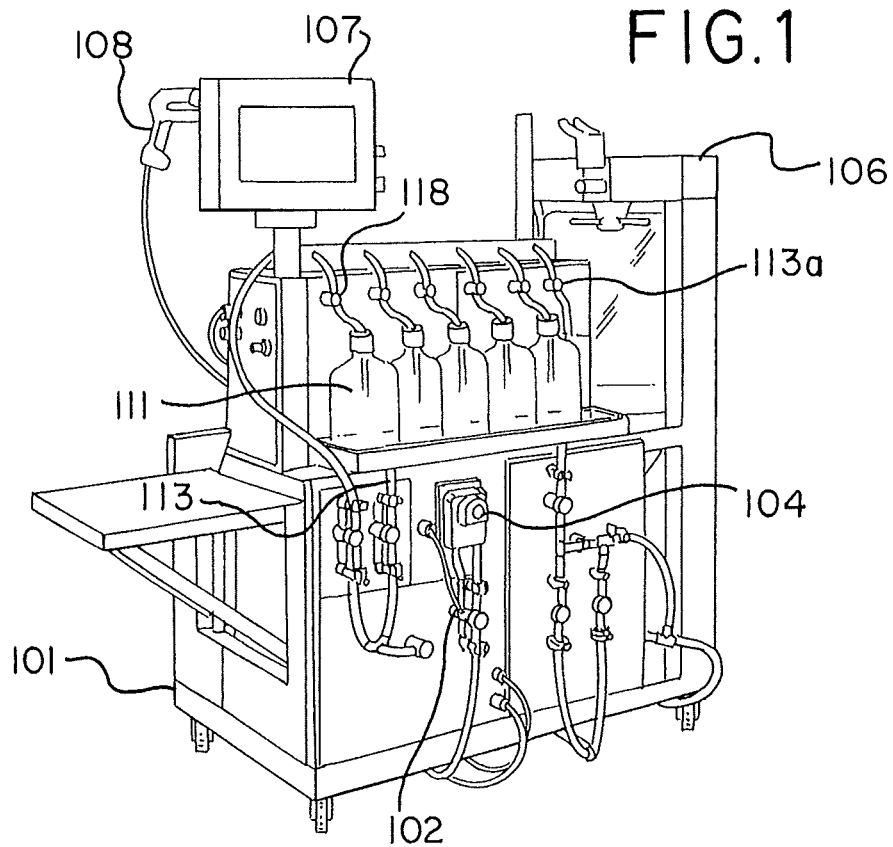
FIG. 1 is a perspective view of a fill and dispense system suitable for applicability with the present system and method.

The embodiments disclosed herein are exemplary only, and the subject matter described herein may be embodied in various forms. Therefore, specific details disclosed herein are not to be interpreted as limiting the subject matter as defined in the accompanying claims.

The present disclosure concerns systems and methods for use in providing assurance of compliance with requirements for proper operation of bioprocessing fluid handling systems that include single-use components or consumables, such as the manifold units of the previously referenced patents and published patent applications. Examples of bioprocessing fluids include biopharmaceutical fluids; preparation and media buffers; water used in making buffers; developmental, clinical and commercial drug products, components and formulations; organic solutions and other organic materials, including cells, tissue, byproduct of cell growth; adjuvants; active pharmaceutical ingredients (API's); antibodies; antibody drug conjugates; vaccines; and combinations thereof.

This system and method could be used for any fluid management system including NFF, TFF, Chromatography, Buffer Preparation, Media Preparation, Dispensing, Transfer Applications and Bioreactors/Fermenters. Examples of biofluids that could be subjected to NFF, including what material would be separated/filtered from another material, are preparation buffer, media buffer, water to be used to make the last two, development/clinical/commercial drug products, organic materials and solutions.

A general function of the disclosure is to ensure that a method and/or system being initiated on an automated, semi-automated or manual basis has the correct consumable installed and is within the operational limits and parameters of that specific consumable for the system or method within which it is to be used or with which it is to be interfaced. A typical consumable has a predetermined function within the system or method. Such systems or methods operate on the bioprocessing fluids and include, for example, NFF, TFF, chromatography typically preparative chromatography, bioreactor applications, media preparation, media dispensing, buffer preparation, buffer dispensing, cell banking, drug or biologic fluid bottling or bagging from bulk containers or other sources, vial filling, blow molding and sealing with drug dispensing, liophilization, biologics flash freeze, cold freeze, cryogenic freeze and combinations thereof.

Typical consumables include manifolds; manifold components; tubing sets; connectors; bags, bottles or containers; reactor bags, bottles or containers; valves; and sensors and/or detectors of pressure, temperature, pump rate, mass flow rate, dissolved oxygen, spectroscopy, near infrared (NIR), fluid flow rate, conductivity, manifold holdup volume, UV, OD, NTU, cell density, cell viability, number of dispense containers and/or bottles and/or bags, amount of resin in a filter column, volume, weight, volume and/or weight of dispense quantity, batch-specific information (e.g. ID, date, etc.), concentration factor, diafiltration volume exchanges, quantity of fluid in container, bottle and/or bag, fractionation information, ERP/MRP information (e.g. Kaban, re-order, customer code, project code, lot traceability, electronic batch record identification, serial number, etc.); and other components for bioprocessing systems that are capable of being manufactured and properly disposed of after a single use or after a number of uses in compliance with the specification for that consumable component when used in the particular system such as a manifold system. These can be presented and/or used in various combinations.

A specific consumable is characterized by at least one readable tolerance specification. Typical tolerance specifications include operational detail, a parameter specification, or combinations thereof. Examples include the model of the consumable; consumable ID; date of manufacture; capacity specifications; pressure specifications; temperature specifications; flow rate or other parameter specifications such as limits, range of operation, safety limits, shelf life, use life (time or volume), time, volume or other parameter logged to date on the component, device or system; number of connections and disconnections; and combinations thereof. Operation parameters include pressure, pump rate, fluid flow rate, temperature, conductivity, manifold holdup volume, UV, OD, NTU, cell density, cell viability, number of dispense bottles, volume of dispense quantity, batch specific information (ID, date), concentration factor, diafiltration volume exchanges, quantity of fluid in bag, amount of resin in column of filter.

Each tolerance specification can be in accordance with the intended use such as type of manifold of the system being assembled and the purpose for which is will be used. A primary objective is to define the suitability of the particular consumable for its intended use and the environment of such use. A readable tolerance specification associated with the specific consumable is provided.

Manifold systems or other consumables typically are designed to interface with the non-consumable, which can take the form of a multi-use device. The interaction between one or more consumables and a non-consumable or multi-use device or devices can be by way of docking, assembly, insertion or other suitable approach. Each consumable can have one or more functions, components or devices, thus being a single-point or a multi-point reference system. The consumables can be considered to have one or more readable tolerance specifications. Each can be associated with one or more specification stages and includes means to record data in a transmittable manner These can be considered as medians for pulling information and can include, for example, bar codes, chips, RFID, engraving, pictures, label, memory key, hard wiring, pattern recognition, system picture inspection through pixel recognition (e.g. of manifold or system), internet enabled transmission and verification (e.g. check sum), cellular per use interrogation with supplier servers and check sum, wireless systems and combinations thereof.

The stored information or data can take the form of an operational detail, a parameter specification, or one or more of each. Various embodiments can have different objectives. One objective for some embodiments is to ensure that only a genuine consumable is being used, such as a fluid management device for that system. For example, after an automated system check, a specific consumable can be recognized as non-genuine for use in that manifold system, and/or it can be recognized as having been used previously in order to lower cross-contamination risk. Non-compliance such as in these examples can be noted, communicated and/or used to prevent use and/or continued use. Thus, the disclosure serves as a check for consumables that are not proper or suitable for the use in the system within which they have been inserted. Previous approaches rely on the operator or user to make the determination if appropriate or not for that particular system. As an example, an operator may have selected the wrong consumable, or tried to re-use a previously used consumable, the present system and method would reject the consumable, the manifold of which is a component, or other device or assembly and will not allow the user to operate the system.

Other objectives of interrogating the consumable include determining whether or not a maximum number of runs allowed for the consumable has been reached and/or the number of runs remaining or expended for consumables with a multiple-runs specification. Other objectives involve probing whether or not an encryption code matches the algorithm of the system. Other objectives include determining whether or not a readable tolerance specification or specifications could be inconsistent with the target or limiting specification or specifications of the consumable. Other objectives include ensuring that the system or method is unable to be used outside of recommended parameters, such as safe tolerances, consumable capacity and so forth. Some embodiments combine multiple capabilities and are directed to multiple such objectives.

The present disclosure decreases the likelihood of operational failure due to incorrectly selecting automated or manual parameters. With the overall approach, the operating system interrogates the consumable through a wired, visual and/or wireless communication. This may include scanning a single bar code or several bar codes, reading a single RFID or several RFIDs, or hand-shaking through a wired or wireless communication protocol to a single or several transmitters and use of other medians as discussed herein. Embodiments can combine one or more such features. Interrogation probes for information stored on a consumable to ensure it is true, complete and specific for the automated system that it is to be used for and/or as a component of.

With the disclosure, in the event the non-genuine or non-approved or out-of-specification consumable is being used on a system, the operating system will communicate this to the operator. In some embodiments, this can result in limiting operation to only a manual protocol.

In a further embodiment, the system can capture information on the consumable so that same is stored in a non-consumable component or some other electronic means for safe storage, manipulation, analysis and/or reporting. Information storage means can be attached to the consumable by overmolding of labels, RFID, transmitters, chips, wires, engravings and so forth with a polymer, alloy etc. through thermal melting, injection and curing, vulcanization, laser welding and/or sealing. Same can include use of a formed clamping device. Typical information in this regard includes serial numbers, lots, manufacturing information, material, and calibration details.

Embodiments achieve equipment parameter verification, automated method activation through an automated physical verification approach, and/or methods to ensure the use of authorized consumable components in the particular system. The operator can choose among application-specific schemes having different objectives in manual operation. The data collection allows traceability information to be safely stored and retrieved as needed.

The present disclosure concerns systems and methods for use in providing assurance of compliance with requirements for proper operation of single-use bioprocessing fluid handling systems, such as the manifold units of the referenced patents and published patent applications. Included are these features, some or all of same in various combinations: (a) This ensures the bioprocessing handling system has the correct consumable (e.g. the disposable components including manifold, its tubing, sensors, containers, bags, valves, sensors, and others as generally noted herein) installed. (b) This ensures the operational parameters are limited to the specification embedded in the system. These include operational limits of the consumable. Examples include: the operator sets an operation pressure that exceeds the upper limit of the consumable; the operator installs a consumable for one procedure (such as tangential flow filtration, TFF) into a normal flow filtration (NFF) unit; and the consumable does not have the needed feedback devices for monitoring compliance. (c) Operational parameters are monitored and operated on by a processor such as CPU, such as pressure, pump rate, fluid flow at a location in the system, temperature, conductivity, manifold hold up volume, UV, OD, NTU, cell density, cell viability, number of dispenser bags/bottles, volume of dispense quantity, batch specific information (ID, date), concentration factor, diafiltration volume exchanges, quantity of fluid in bag(s), amount of resin in filter column. (d) The system includes a reference system (spec storage device or median device, e.g. chip, RFID, barcode, engraving, label, etc.) that has one or multiple such devices. The specs are the application and/or operation limits of the consumable of the particular system. (e) The system includes a reader for the spec storage device, reading medium examples being photo eye, RFID transmitter/receiver, barcode scanner, Bluetooth transmitter/receiver, wireless transmitter/receiver, hardwired communication transmitter/receiver. (f) The operating system interrogates the system for compliance of these specs etc. (g) The system and method ensure an operator and/or automated system is unable to use the system outside the recommended safe tolerances, or ensure the device is genuine, by engaging interlock(s) when out of compliance. (h) This creates an electronic batch record for the consumables being used.

Interlock objectives, when desired and provided, include the following. Interlocks can occur when the operating logic detects operation that is inconsistent with the readable tolerance specification or specifications. For example, an interlock can activate a signal to inform of non-compliance of the consumable. An example has the interlock activate a stoppage function with respect to the manifold system capable of avoiding out-of-compliance operation. Other examples include having the interlock not allow operation through software logic, electromechanical contactor logic, relay logic, visual and/or audio-indication, and combinations thereof.

A "non-genuine" or "non-approved" consumable is one that is not in line with requirements, including these, for example: A manufacturer and/or equipment-specific fluid management processing system such as in applications as noted herein is out of conformity with its specific design to work with optimized and/or approved consumables (fluid management device) with the processing system. A device is non-genuine or non-approved according to what the manufacturer deems inappropriate to work with the processing system. Specific examples are as follows: example 1 of using a consumable that is designed for TFF on a NFF system; example 2 wherein a TFF manifold designed for 15 pounds of pressure operation but an operator initiates a set point of 60 pounds of pressure; and example 3 checking whether or not a TFF manifold designed for a manufacturer's equipment is correct, or a system is assembled without needed feedback devices.

The reference system is a specification storage device (memory chip, barcode, engraving, label, etc.) that is read via different mediums (photo eye, RFID transmitter/receiver, barcode scanner, Bluetooth transmitter/receiver, wireless transmitter/receiver, hardwired communication transmitter/receiver), and combinations thereof. A single or multipoint is defined as the number of devices used on the consumable to transmit the information. The advantage of the multipoint is to have redundant and/or overflow of specifications to read. Multipoint can mean providing redundant points (check sum), multiple points to read from, such as multiple means of reading or multiple different types of reading means. Multiple point reads can indicate correct location of a component within the system. The objective is to minimize the possibility of installing similar parts (which can be a single component or a multi-component part) in incorrect locations of the system.

The systems, devices and methods of the present disclosure need not be limited to inclusion of devices that are gamma stable i.e. the disclosure does not require an electronic system on the consumable that would need to survive gamma irradiation. Examples are ethylene oxide, autoclave, chemical sterilization, or not sterilizing at all.

Application specific methods or recipes include:
(a) constant rate NFF; (b) constant pressure NFF; (c) R-P stat method NFF; (d) Manual, which is the only method that could run if a non-genuine consumable was being used on the system; (e) Integrity test; (f) dispense; (g) chromatography; (h) constant rate TFF; (i) constant pressure TFF; (j) simultaneous constant rate and constant pressure TFF using a control valve or pump; (k) simultaneous constant rate and constant pressure TFF using a control valve or pump then switching to constant pressure control via pump; (l) buffer preparation; (m) media preparation; (n) volume transfer; (o) weigh transfer; (p) bioreactor and (q) fermentation.

Static operation and/or static filtration operation can be practiced in association with the disclosure. Also contemplated are dynamic operation and/or dynamic filtration. Typically a dynamic approach is practiced when filtration was not originally planned for a system or method, such as adding filtration capability to a manifold. In such instances software compensates for the additional filtration requirement.

Figure 2:
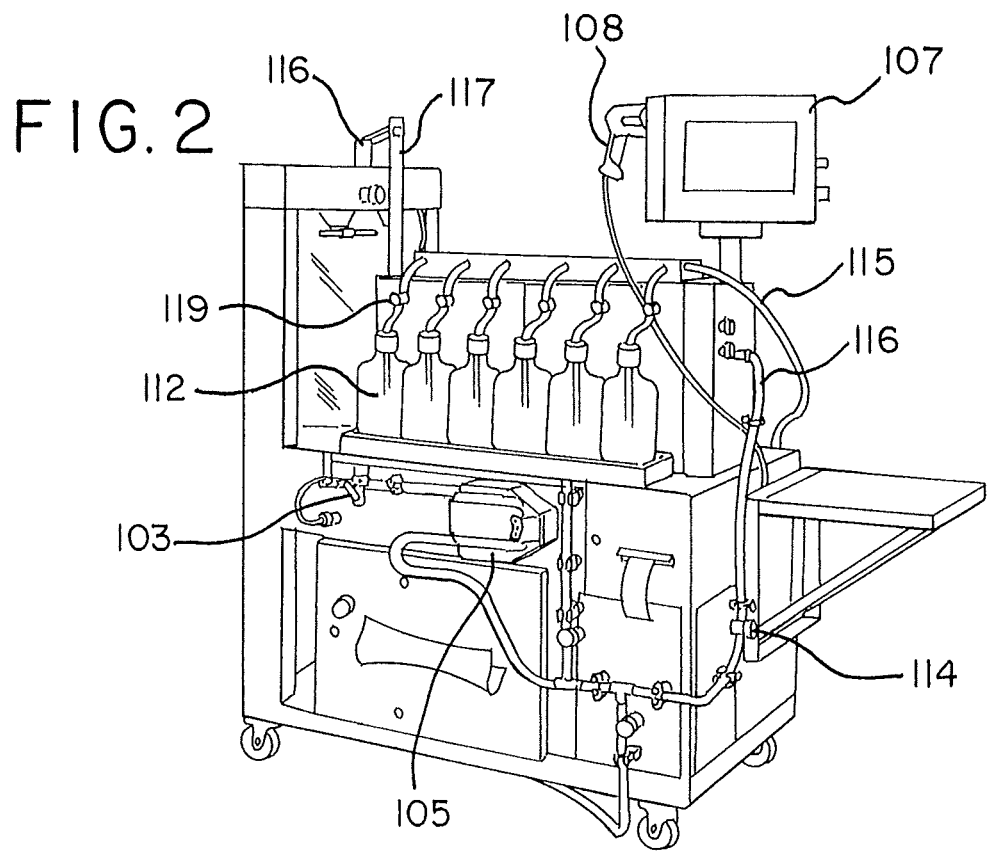
FIG. 2 is a further perspective view of the system illustrated in FIG. 1.

FIG. 1 and FIG. 2 illustrate an embodiment of a fill and dispense system within which the disclosure materials are suitably incorporated. Included in this illustration is a cabinet 101, dispense pressure sensor 102, filtration pressure sensor 103, dispense pump 104, filtration pump 105, weigh station 106, control panel 107, such typically including a touch screen display or other communication means, and a median component 108 (e.g. a bar code scanner). Also included is a processor (not shown) including software or control logic for manifold operation, operations of loading, administration and data collection. While the median for pulling information 108 is a bar code scanner, other median systems as discussed elsewhere herein are suitable for pulling information used as the boundary conditions in following the automated parameter assurance system and method of this embodiment.

This particular embodiment shows multiple supply containers 111 and collection containers 112, each of which can be bags, bottles or other containers. Also shown are valves which can be components of different modules and can function within a chase module (including a chase air input 113 and chase valve 113a), a module with a sample location and for integrity testing and purge air system (including valve 114 for integrity test and purge air input). A process air regulator 115 and a process air output passage 116 (such as a tube length) are shown. A spine vent 116 and stack 117 are shown in FIG. 2. Fluid passage with respect to containers 111 is regulated by respective valves 118, and fluid passage with respect to containers 112 is regulated by respective valves 119. These containers, valves, sensors, tubing, passageways and other components are exemplary consumables of FIGS. 1 and 2.

Figure 3:
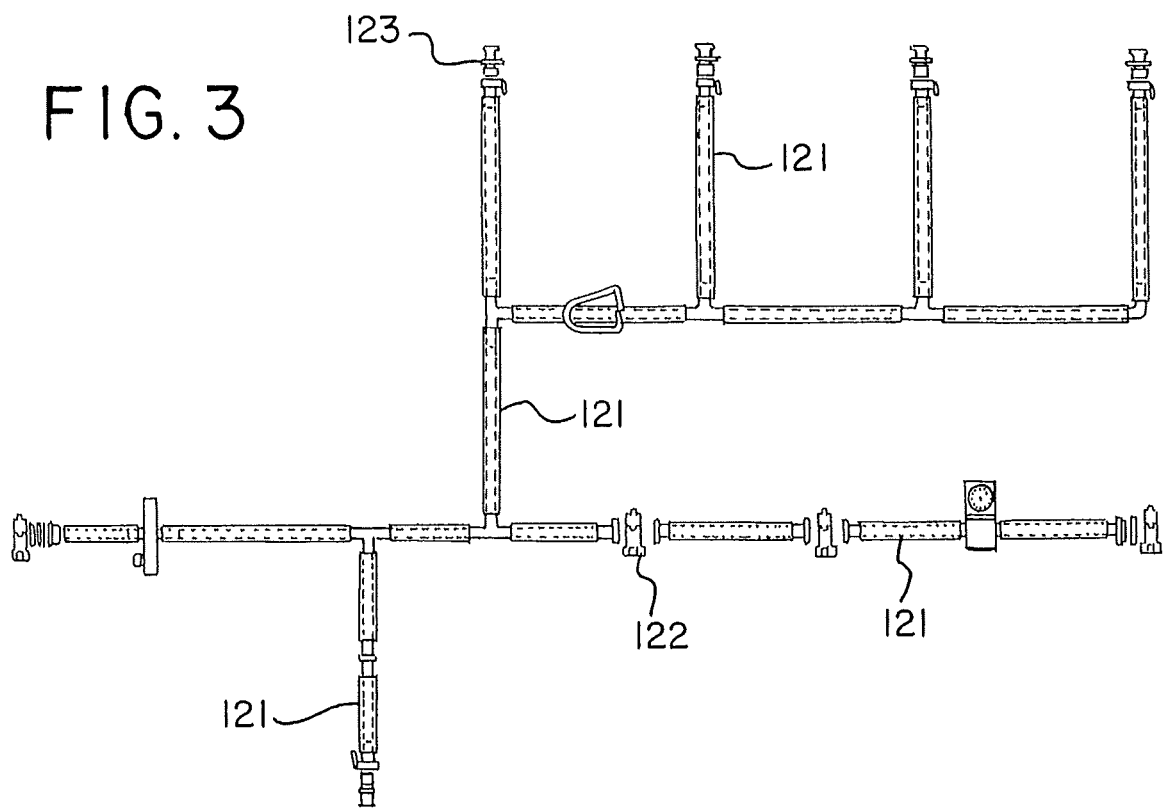
FIG. 3 is a plan view of an embodiment of a filtration manifold assembly.
Figure 4:
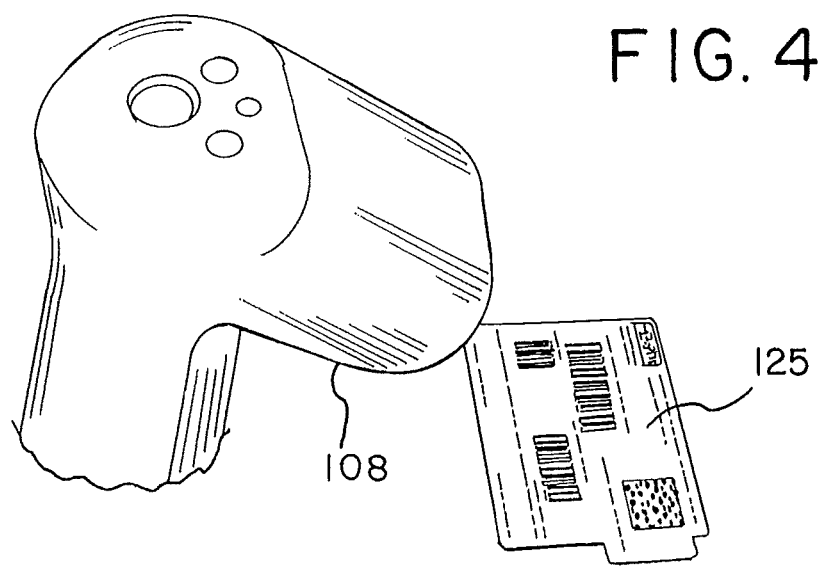
FIG. 4 is a perspective view showing a sterilized packaged component with a barcode being read by a reader of a system embodying the disclosure when the median is a barcode.

FIG. 3 provides an example of a filtration manifold of the type that can be incorporated into systems according to the present disclosure. The system is modular in that a plurality of channels, typically of tubes 121 are joined aseptically, such as by connectors 122. End connectors 123 aseptically join a tube component to a container such as 111 and/or 112 in FIG. 1 and FIG. 2. One or more sensors 124, such as pressure sensors, are positioned within the manifold. FIG. 4 illustrates a disposable with a bar-coded label being scanned by the scanner 108.

Figure 5:
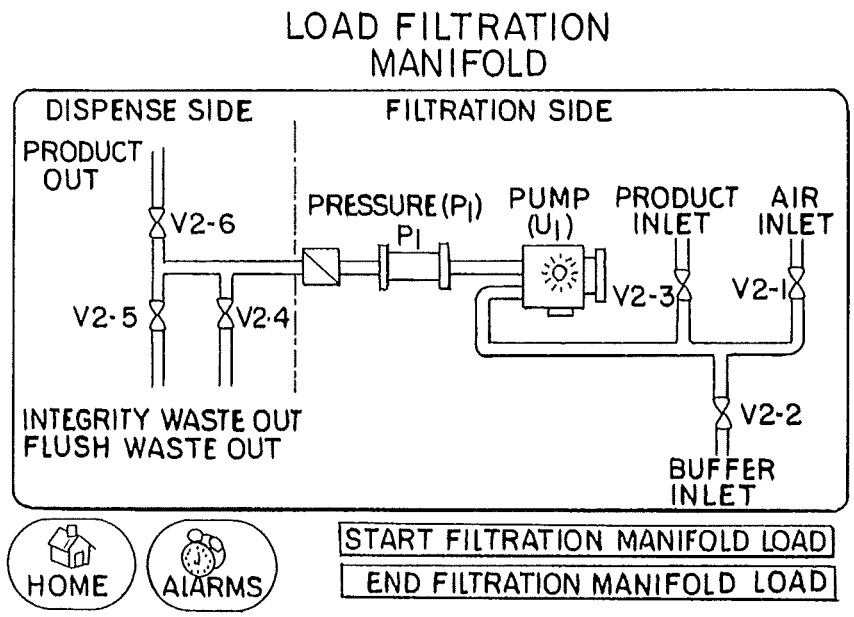
FIG. 5 is a schematic of a load filtration manifold display associated with a step-wise method with user prompts to load a static filtration manifold.
Figure 6:
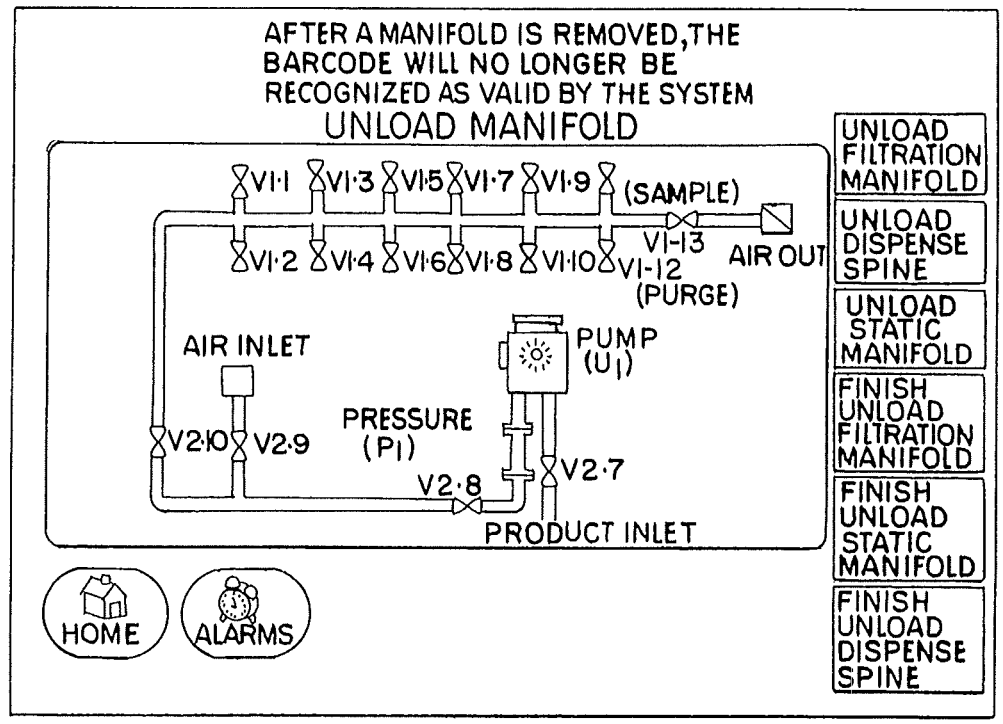
FIG. 6 is a schematic unload manifold display concerning a step-wise method with user prompts to load the static dispensing manifold, and at stack loading of the dispensed manifold, the pinch valves open to allow insertion of dispense tubing.

The load filtration manifold display of FIG. 5 has a step-wise method with user prompts to load a static filtration manifold. Valve icons can change in appearance to indicate opening, closing and so forth. The FIG. 6 upload manifold display embodiment can have a step-wise method with user prompts to unload the static manifolds and choose whether to unload a filtration or dispensing manifold. In a feature, once the "finish unload" button has been pressed, that particular manifold cannot be re-scanned into the system, and a new manifold will need to be installed before further use. A launch page allows operators to have the ability to create, store and modify methods for the automated execution of filtration and dispensing processes. For example, the user can be presented with a number of options such as filtration, flushing, air purging and integrity testing.

At the FIG. 7 display, method maintenance gives the operator the ability to modify or delete stored methods in the system, which can include parameter field populating with stored values for the chosen method. The FIG. 8 flush page typically launches a parameter table and storage method screen for creation and storage. In an air purge mode, operators are able to create and store filtration manifold air purge methods. A product filtration page can be provided to launch a parameter table and a storage method screen for creating and storing product filtration methods. Typical modes of filtration able to be selected are: constant rate, constant pressure, and rate/pressure stat to pump fluid to the filter and run it at a constant rate until accumulated material on a filter causes back pressure to exceed a user-defined value, resulting in feed rate reduction to maintain the pressure under the designated limit.

Integrity test information is illustrated in FIG. 9 whereby a parameter table is launched and operators are able to create and store filter integrity test methods. This allows an operator to enter integrity test values for test duration, filter wetting fluid, feed pressure and a downstream container or consumable to be used. Integrity testing provides instantaneous "average over duration" readings of a diffusional flow rate. When concerned with filters, integrity testing can incorporate test parameters from the filter manufacturer.

Figure 10:
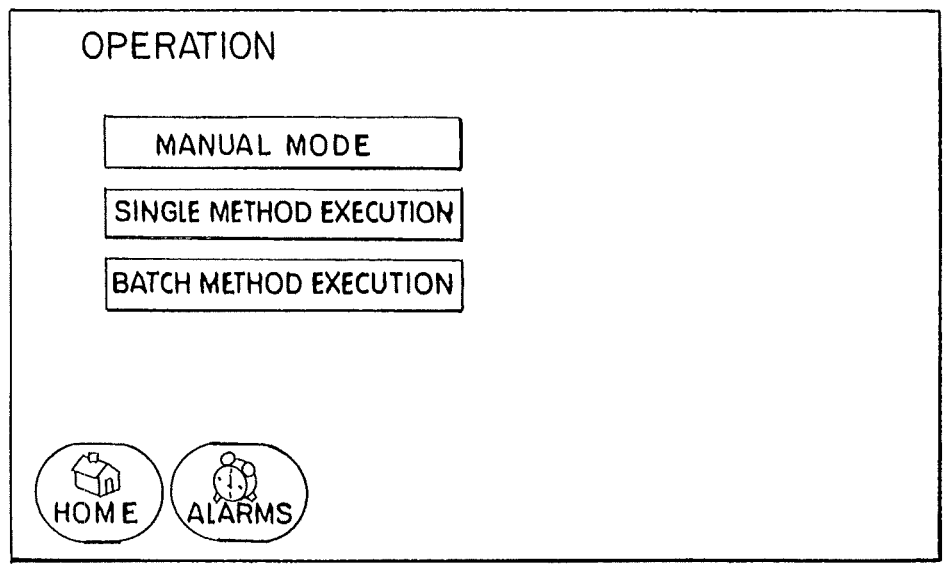
FIG. 10 is a schematic illustration of a display of an operation page as the launch page where operators have the ability to load recipes and execute them through, for example, a manual mode, a single method execution mode, and a batch method execution mode.
Figure 11:
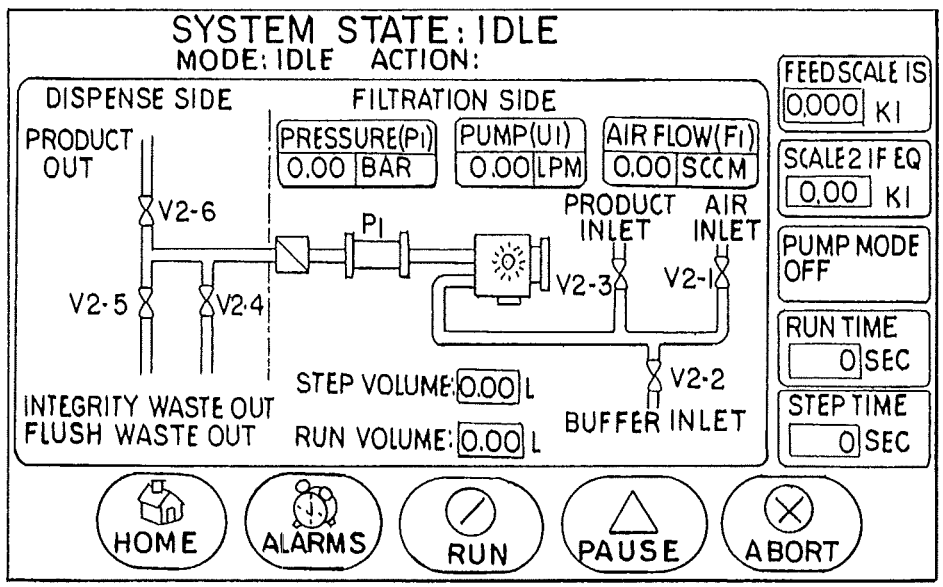
FIG. 11 is a schematic illustration of a run screen allowing a user to commence a method sequence.

The FIG. 10 operation page is a typical launch page. FIG. 11 illustrates a run screen for commencing a method sequence, illustrating fluid processing, and display in a single area. Exemplary information includes read-in values from devices, set point values to devices, alarms, interlocks, recipe parameters, and calculated values. Typically, no recovery paths are built into the flow path. If any interlock were to occur, the system will halt, go into idle and wait for the condition to be corrected before the operator can continue the sequence.

Figure 12:
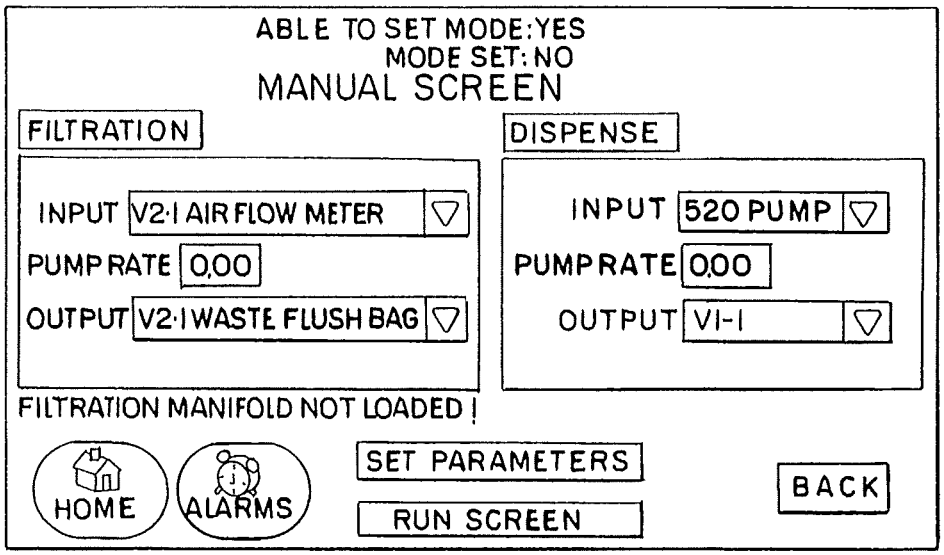
FIG. 12 is a schematic illustration of a manual screen display as a template for operation of the system without a predetermined stored method.
Figure 13:
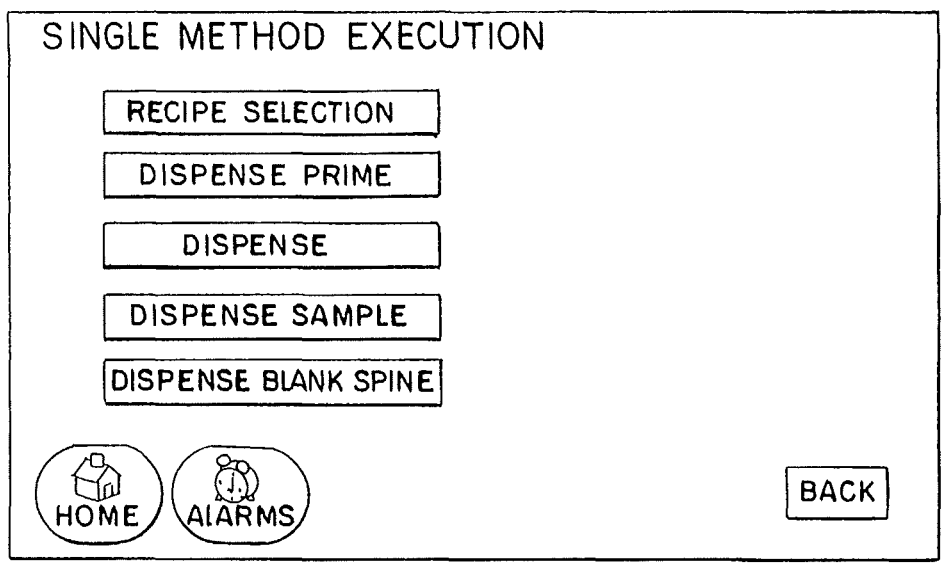
FIG. 13 is a schematic illustration of a single method execution display to launch a page where operators have the ability to load a single automated filtration or dispensing system and practice its method, allowing for access to multiple dispense methods.
Figure 14:
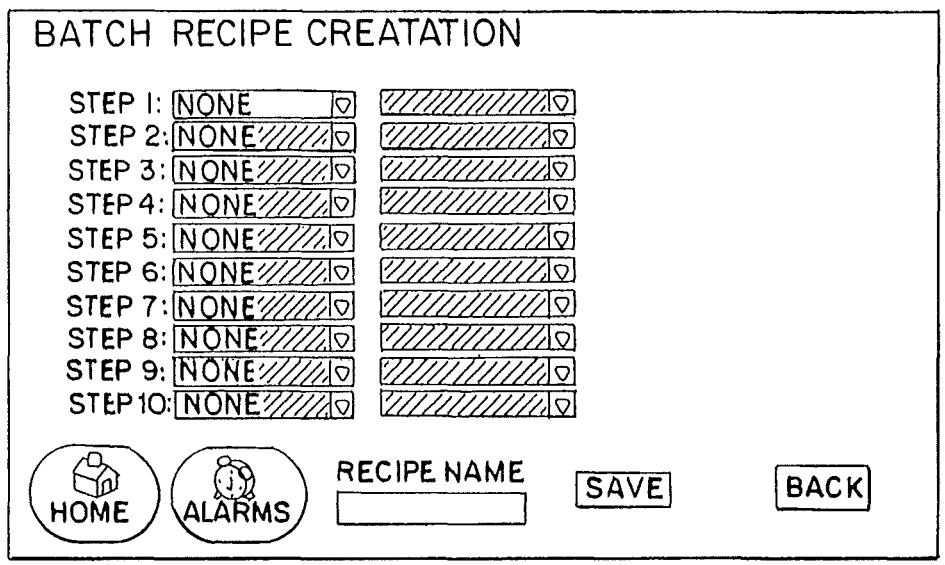
FIG. 14 is a schematic illustration of a batch recipe creation display.
Figure 15:
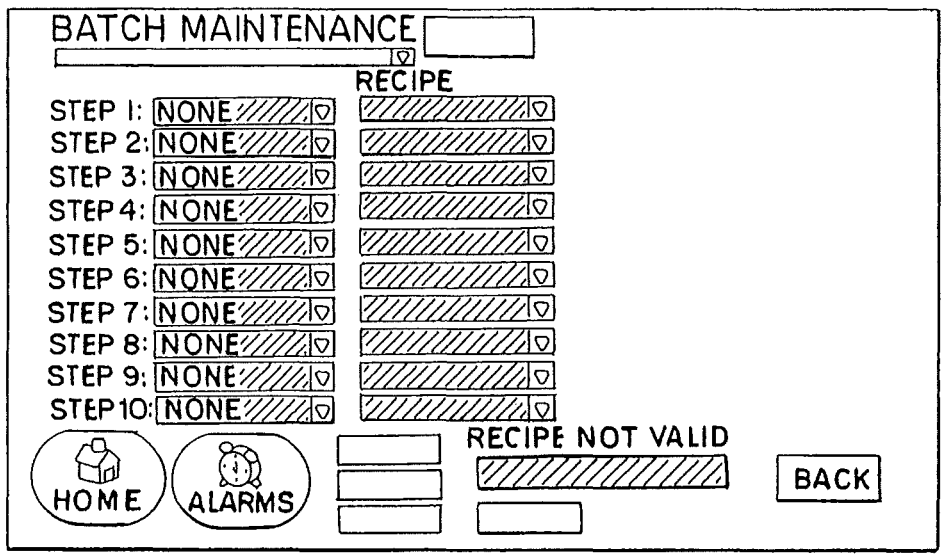
FIG. 15 is a schematic illustration of a batch maintenance display.
Figure 16:
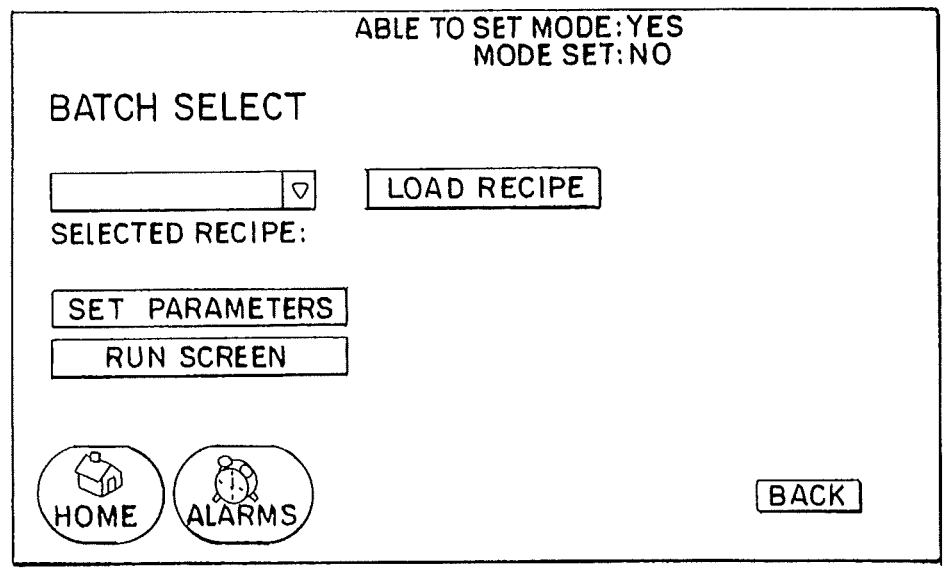
FIG. 16 is a schematic illustration of a batch select display for batch method execution allowing operators to run a complete sequence of operations to complete a batch process.

A manual mode option is illustrated in FIG. 12, allowing system operation without a predetermined stored method. This mode is bound by flow paths but not individual valve operation and is useful for testing and verifying flow paths and can be used for clearing a flow path for product recovery if needed. This will not interlock if high pressure is created, but it will prevent undesirables such as pumping against a closed valve. The FIG. 13 single method execution page displays when allowing a single automated filtration or dispensing method. Batch recipe or protocol creation and batch maintenance are illustrated in FIG. 14 and FIG. 15, respectively. Batch method select execution is illustrated in FIG. 16, allowing operators to run a complete sequence of operations to complete a batch process.

Figure 17:
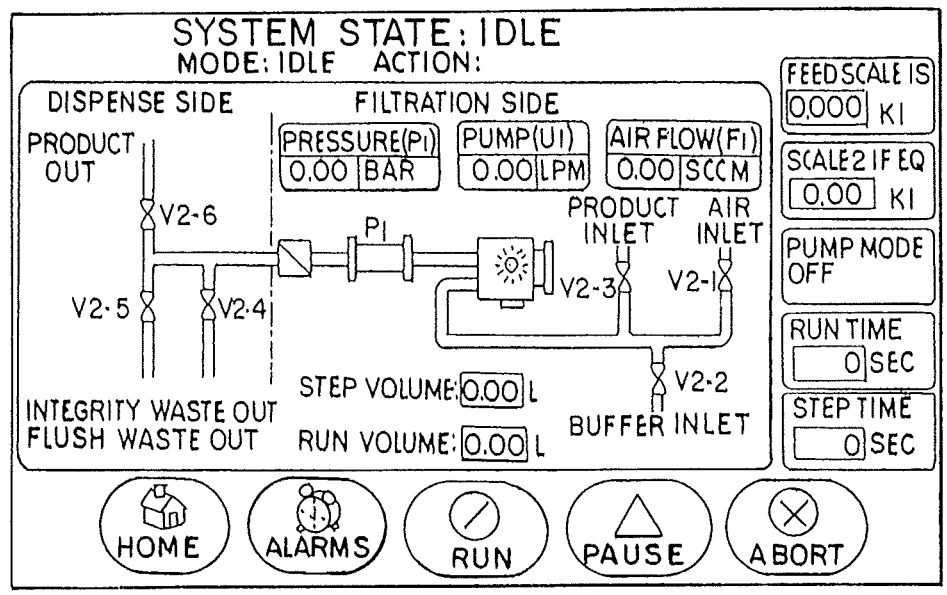
FIG. 17 is a schematic illustration of an idle system state display.
Figure 18:
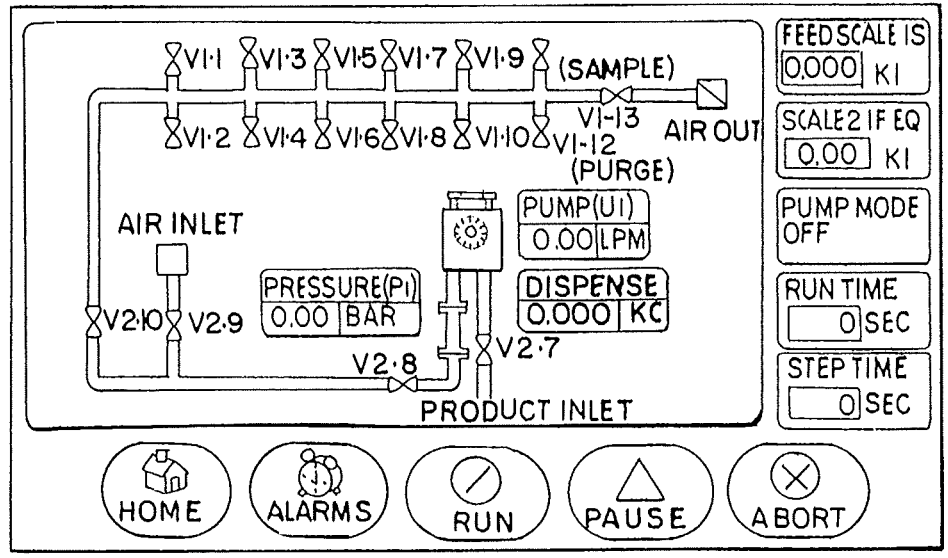
FIG. 18 is a schematic illustration of an idle system state display for a sequence of operations as they are executed and includes operator prompting where inputs or confirmation are appropriate.

FIG. 17 and FIG. 18 show a display for an idle system state. Typically at this stage all valves are closed. This moves to prime a preset volume of fluid. A dispense page can be provided to display the sequence of operations as they are executed and, where appropriate, prompt the operator for inputs or confirmation. In this regard, alarm settings are illustrated in FIG. 19, allowing the operator to modify alarm parameters, including in/out flow, pressure, temperature and/or conductivity, when included in the system. FIG. 20 illustrates constants to allow an administrator to enter or modify programmed constants tied to the software being run. This allows limitations to be set for working parameters so the operator cannot set values exceeding same. Trending can be monitored as illustrated in FIG. 21. Examples include monitoring flows, pressures and weights of input and of product.

The system and method can follow various schemes or recipes. These include the following. Constant rate NFF maintains rate, monitors pressure and ensures pressure does not exceed a set point. Constant pressure NFF maintains pressure, monitors rate, and ensures rate does not exceed a set point. Rate/pressure stat method NFF maintains a flow rate until pressure set point is reached, at which stage the system will switch to pressure control reducing flow rate until the user-definable limit is reached. Manual operation allows the user to define a motor set point, inlet valve set point, directional valve control set point and manual prime function. An integrity test pressurizes the filter manifold with filter manufacturer recommended pressure for diffusion testing, with rate of diffusion being checked and validated as appropriate. Dispense has aliquots and number of samples programmed based on the available manifold.

Embodiments include NFF that automatically monitors, adjusts and documents pre-filter back pressure and flow rate to optimize filtration speed, maximize filter throughput, and eliminate the need for constant supervision during filtration runs. Integrity testing can be included to check the sterilization grade filter post filtration process, using a sterile air source connected to a thermal mass air flow controller.

Dispensing embodiments volumetrically or gravimetrically dispense solutions to containers, bottles, bags or other consumables. Median readers scan or otherwise capture data stored, typically on the consumables or packaging or labeling for same, for indicating properties. An example uses a barcode reader which can identify parameters such as tubing size, container size, total number of a type of consumable, and so forth. Typically, this information becomes parameter value limiters (maximum and/or minimum) for the recipe or protocol entry. Results include automatically dispensing solution into the containers having their corresponding labels and medium.

Figure 22:
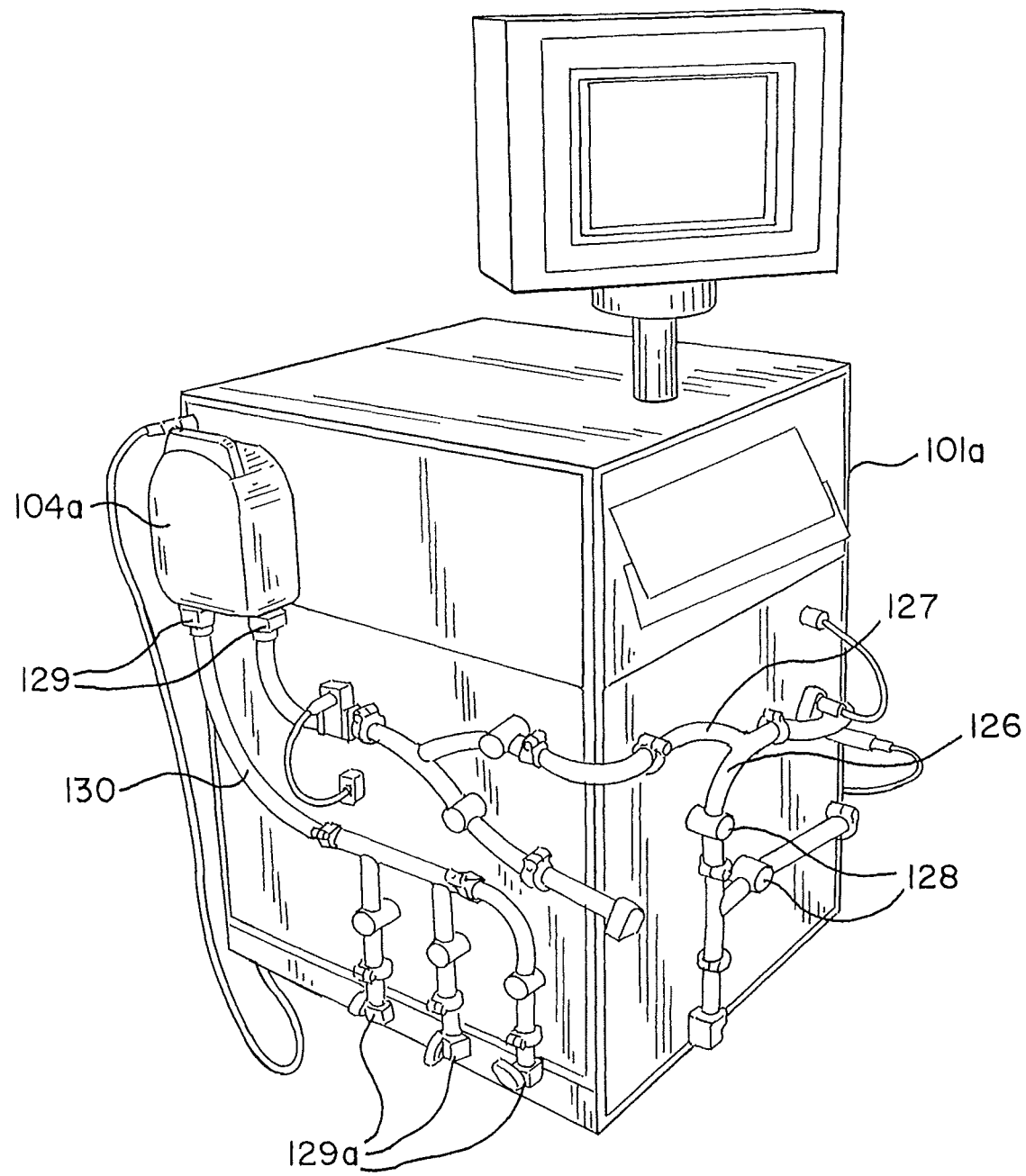
FIG. 22 is a perspective view of another fill and dispense system with a manifold that can be suitable for achieving NFF strategies.

FIG. 22 illustrates an embodiment of a system and illustrates a manifold arrangement which can be suitable for NFF strategies. This embodiment includes a network of connected passageways, shown as tubing in this FIG. 22. Included are cabinet 101a, control panel 107a associated with median reading, dispensing pump 104a, upstream manifold 126, each manifold having tubing lengths 127, valves 128 and connectors including pump connector 129. Downstream manifold 130 includes connectors, including pump connector 129 and other connectors 129a for receiving containers (not shown in FIG. 22). Any of these components can be a consumable with one or more median components allowing the parameter assurance of this disclosure.

Figure 23:
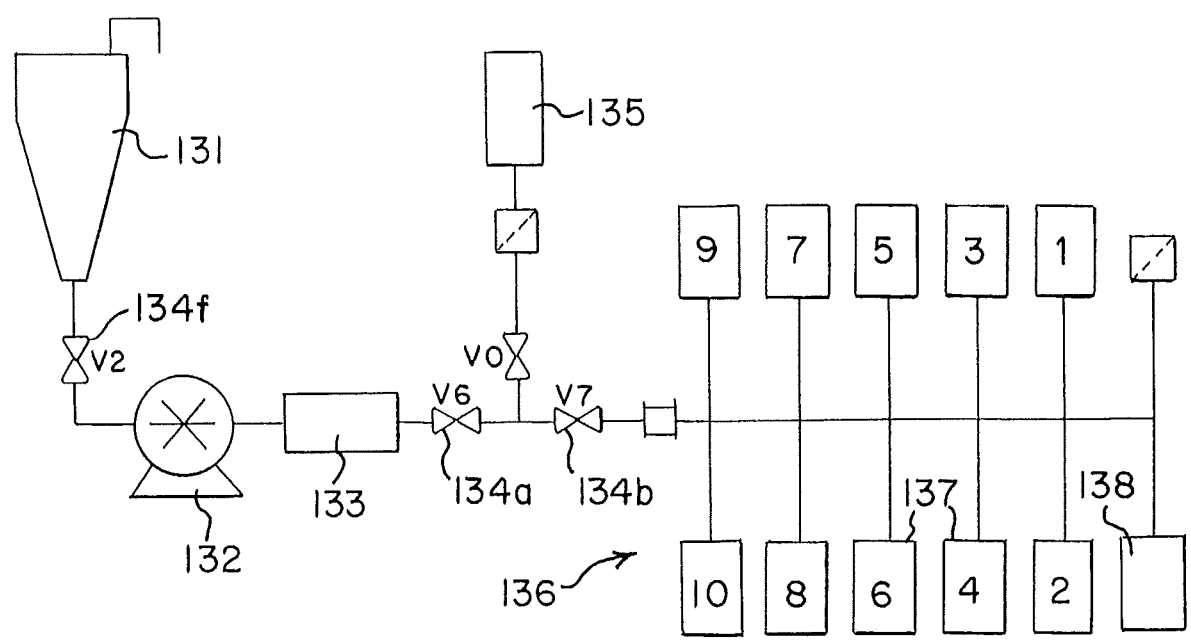
FIG. 23 is a schematic illustration of a system with a manifold having consumables according to the present disclosure.

FIG. 23 provides a schematic of a full process for preparation, including a bioprocessing container (BPC) 131, pump 132, pressure sensor 133, upstream valve (V2) 134f, downstream valves (V6, V7, V0) 134a, 134b, 134c, gas flow meter 135, and a manifold (generally designated at 136) having multiple containers 137 (labeled 1 through 10) and a quality-control container 138.

Figure 24:
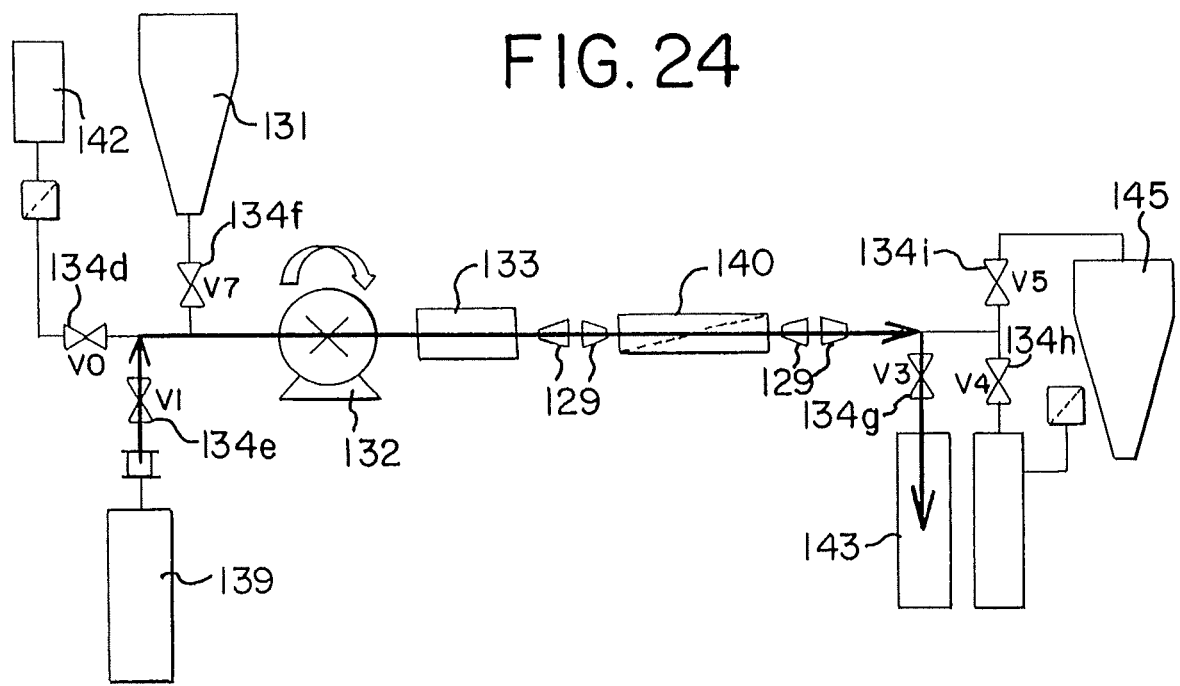
FIG. 24 is a schematic illustration of step 1 of the full process for a system generally as illustrated in FIG. 23, illustrating flush.

FIG. 24 illustrates step 1 of this system in which the operator aseptically attaches flush solution source 139 to the system at a location just upstream of the bioprocessing source or container 131. The flush sequence recipe or protocol is initiated by the operator or automatically, facilitated by gas flow meter 142 and valves (V0', V1 and V2) 134d, 134e and 134f. For example, step 1 proceeds with valve 134e open and valves 134d and 134f closed. Then, the flush solution is aseptically removed from the system after passing through and flushing the filter 140 and into waste process container 143 with valve (V3) 134g open and valves (V4, V5) 134h and 134i closed.

Figure 25:
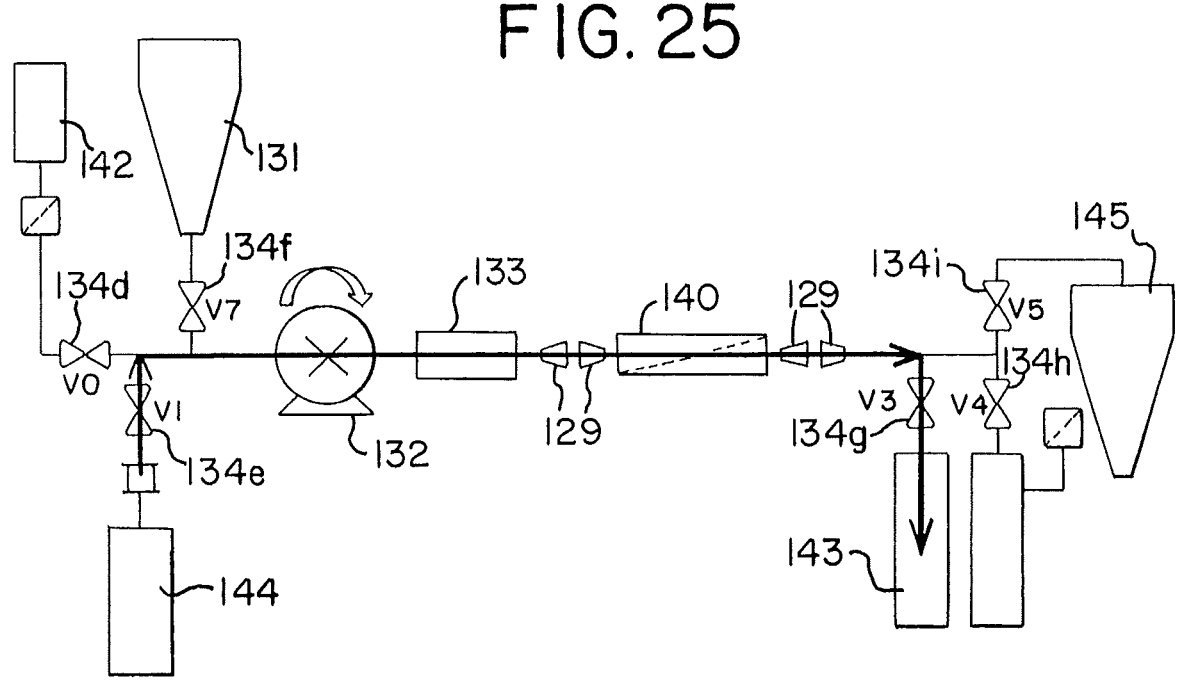
FIG. 25 is a schematic illustration of step 2 of the FIG. 21 system generally illustrated in FIG. 23, being an equilibrate step or procedure.

Equilibration proceeds in step 2 according to FIG. 25. The operator aseptically attaches equilibration solution to the system from a solution source or solution container 144. Inflow of equilibration solution is closely upstream of the input or retentate BPC 131, facilitated by gas flow meter 142 and valves (V0', V1 and V2) 134d, 134e, 134f. Equilibration solution after having passed through the filter 140 is collected and aseptically removed downstream of the filter and upstream of the receptor or filtrate BPC 145.

Figure 26:
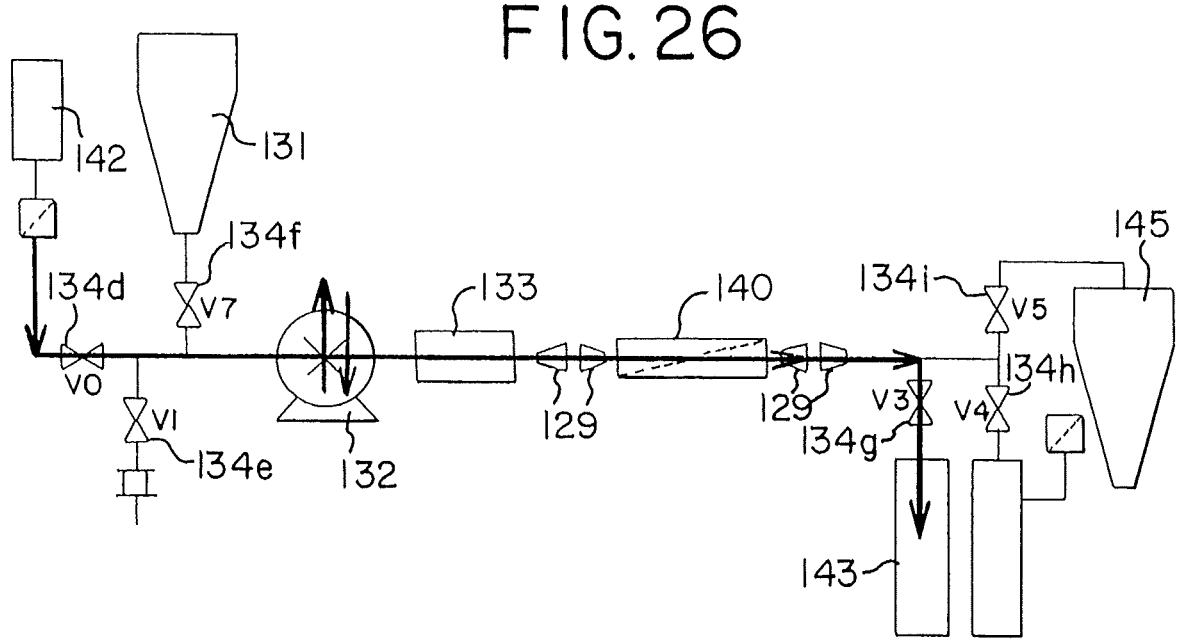
FIG. 26 is a schematic illustration of step 3 of the system generally illustrated in FIG. 23, being an air purge waste step or procedure.

FIG. 26 shows the step 3 air purge which follows a path similar to step 2 during which flow restrictions are lessened or removed. For example, when pump 132 is a peristaltic pump, its front head rollers are opened. A recipe-based line purge is initiated by operator or automatically, the impetus for the purge being from the gas flow meter, with the material purged from the system being moved to the waste process container 143 or outflow. Then the peristaltic head, if a peristaltic type pump is used, is subsequently closed, or the system is again moved to full operation. In this step 3, typically valve 134d is open and valves 134e and 134f are closed.

Figure 27:
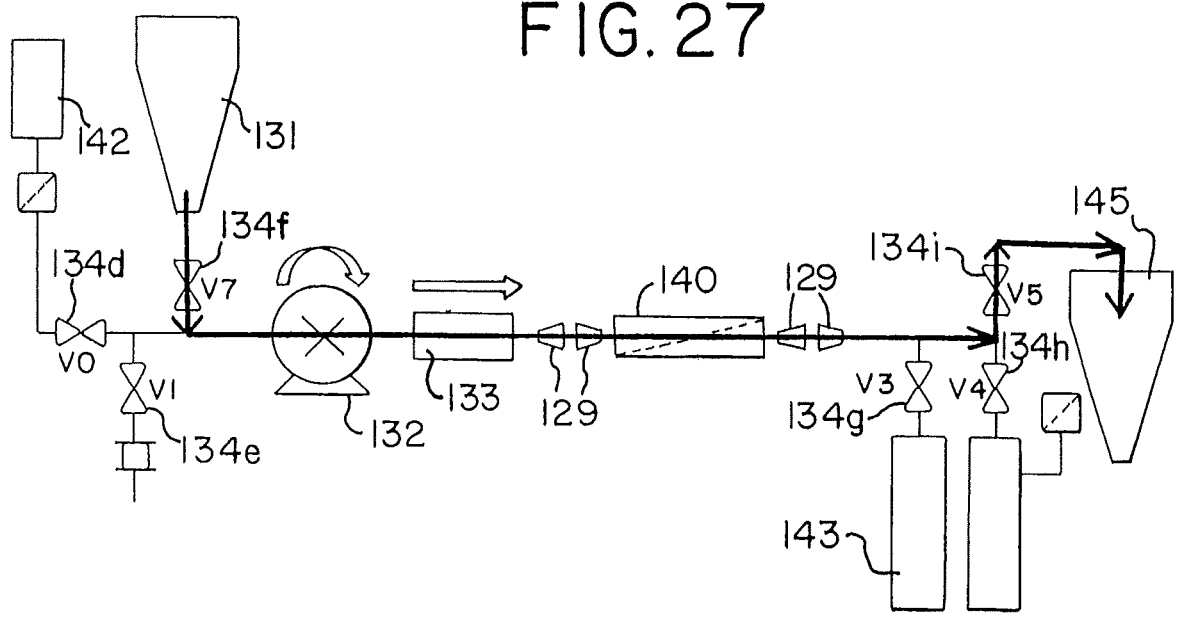
FIG. 27 is a schematic illustration of step 4 of the system generally illustrated in FIG. 23, being a filtration step or procedure.

Filtration proceeds as illustrated in step 4 of FIG. 27 wherein a recipe-based filtration sequence or protocol is operator or automatically initiated, typically with valves 134f and 134i open and valves 134d, 134e, 134g and 134h closed. Then the bioprocessing solution is pumped from the bioprocessing fluid container or source 131, monitored, filtered and collected in the downstream BPC or bioprocessing solution collector 145 which can be a container as shown or a conduit or other means for receiving filtered fluid aseptically. This sequence completes based on pressure monitoring for achievement of a maximum or other threshold pressure, gravimetric feedback or operator control. For example, pressure can be monitored and controlled by a single-use pressure sensor preventing over-pressurization of the filter.

Figure 28:
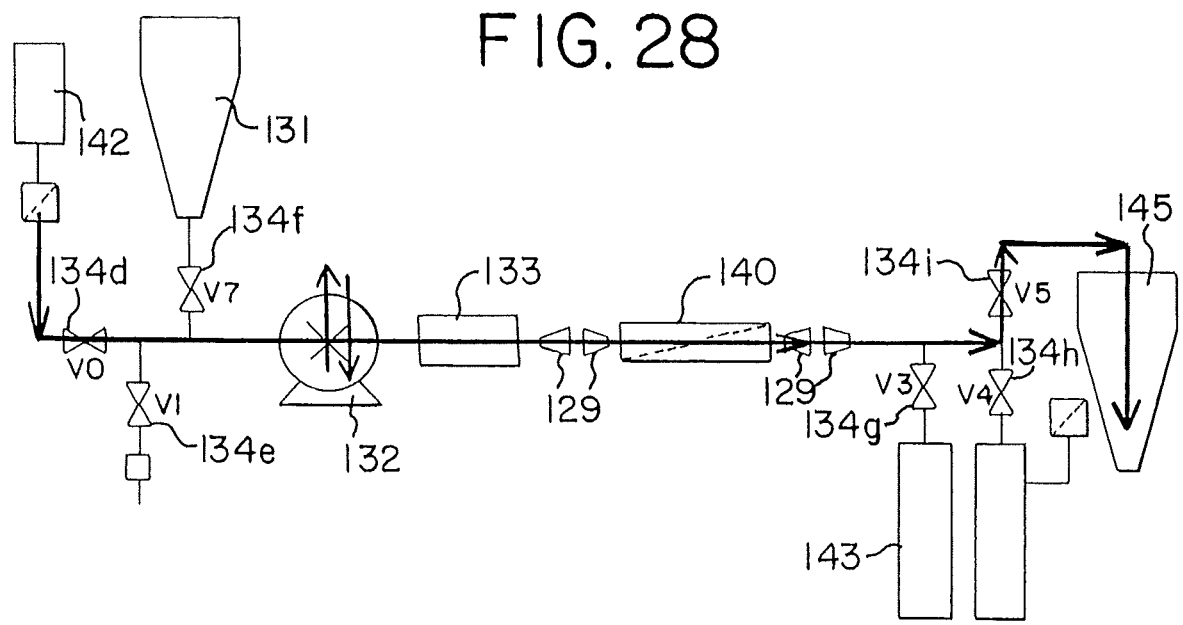
FIG. 28 is a schematic illustration of step 5 of the system generally illustrated in FIG. 23, being an air purge product step or procedure.

Product air purge can be carried out as illustrated in FIG. 28 as a step 5 with gas or air source including the gas flow meter 142. Flow restriction adjustment proceeds and then the system is brought back into operation. For example, when a peristaltic pump is included, the pump head rollers are opened. A recipe-based line purge to product collector 145 in initiated automatically or by operator choice. For example, valves 134d and 134i are open and valves 134e, 134f, 134g and 134h are closed, and purge by air or other gas proceeds to collect residual product in the system. Once the sequence completes, the peristaltic head is closed as needed.

Figure 29:
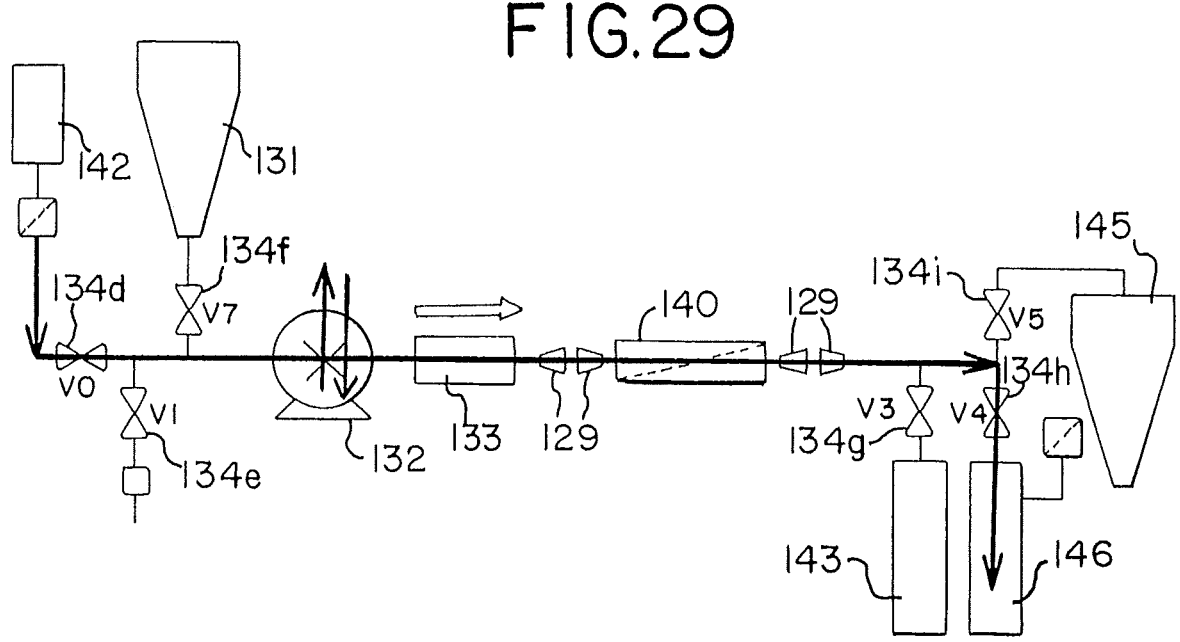
FIG. 29 is a schematic illustration of step 6 of the system generally illustrated in FIG. 23, being an integrity test step or procedure.

Integrity testing can be carried out as a step 6 as shown in FIG. 29. With this integrity test, the pressure is monitored, and the gas flow meter 142 monitors diffusion across the filter 140, with valves 134d and 134h open and valves 134e, 134f, 134g and 134i closed. Flow restriction adjustment proceeds and operational pumping is re-established after this integrity test. During the test, preprogrammed pass/fail values are provided in the control logic to indicate results of the operator-initiated or automatic test. If a filter passes the integrity test, the solution is sampled and stored and/or dispensing begins. If the filter does not pass the integrity test, the process needs to be repeated, and the downstream BPC container or collector 145 acts as the original retentate container or source 131.

Figure 30:
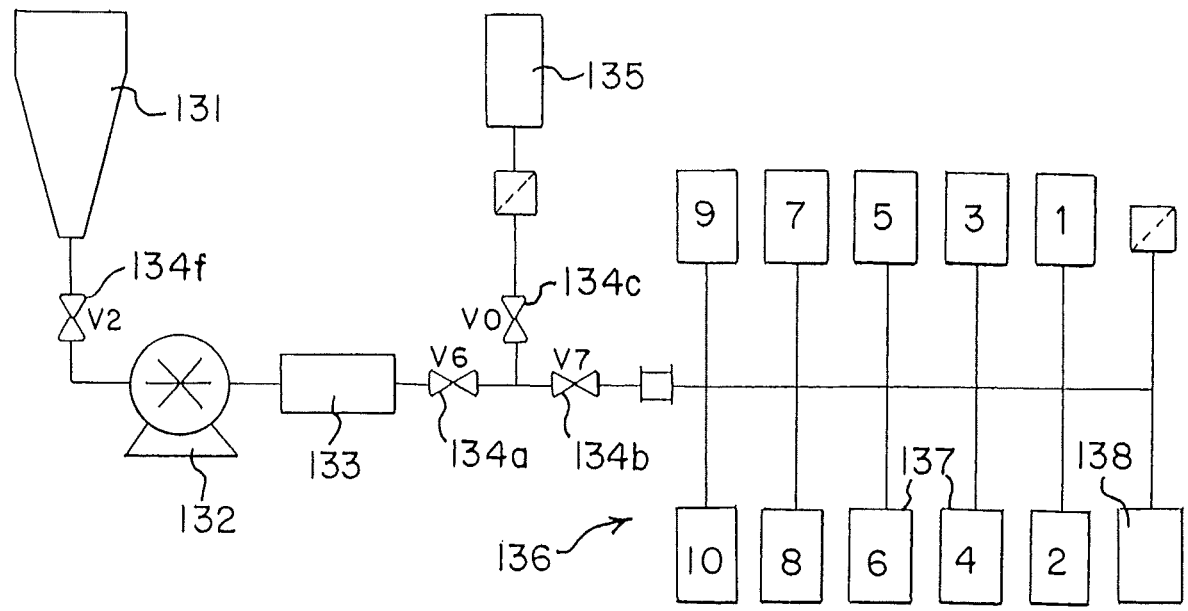
FIG. 30 is a schematic illustration of preparation or set-up which can be useful for a FIG. 23 system.
Figure 31:
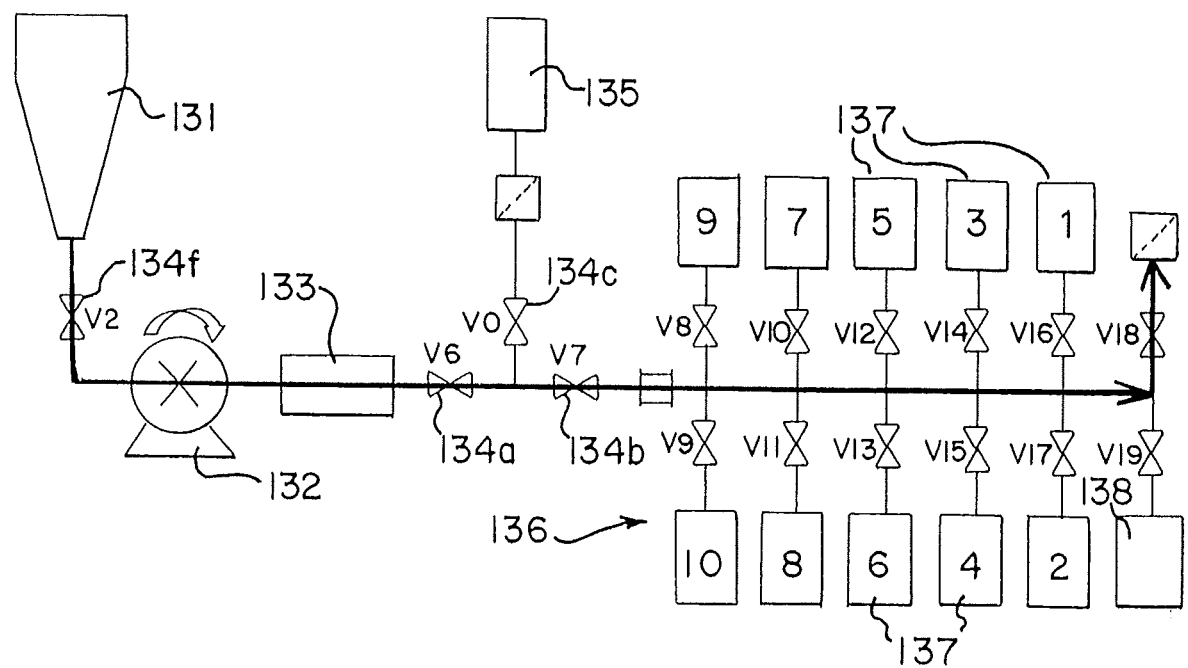
FIG. 31 is a schematic illustration of filling or priming that can be useful for a system as in FIG. 23.
Figure 32:
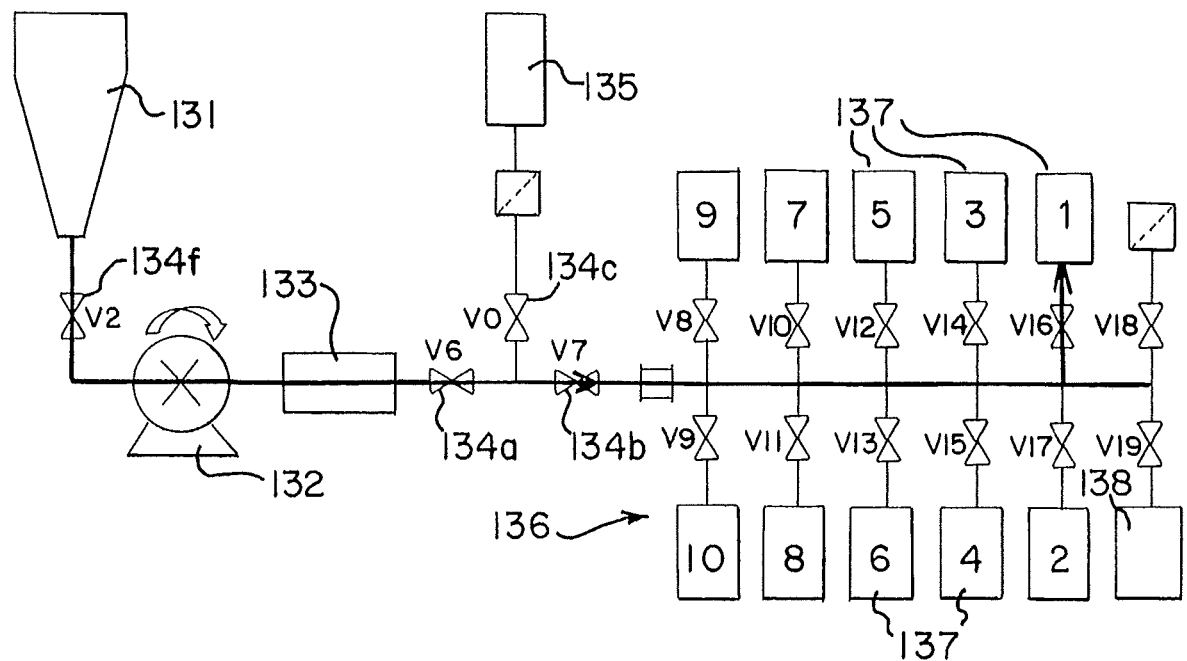
FIG. 32 is a schematic illustration of filling, fill, which can be useful in a system of the type illustrated in FIG. 23.
Figure 33:
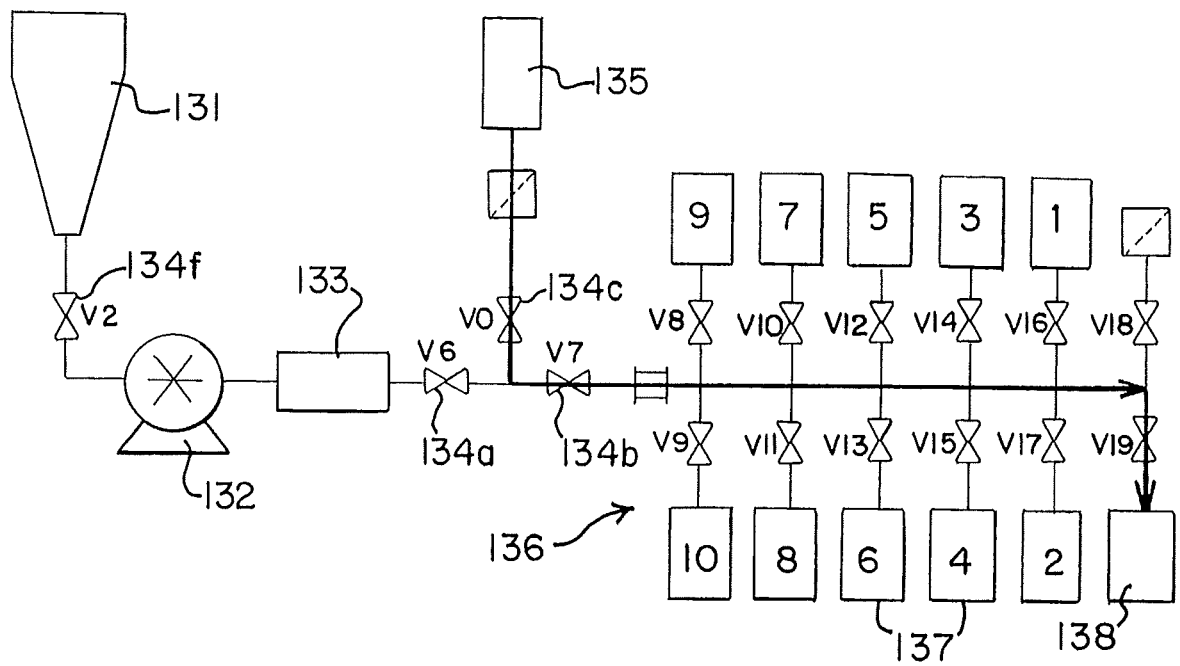
FIG. 33 is a schematic illustration of filling, complete recovery, useful in a system as generally illustrated in FIG. 23.

Preparation setup for this multi-step embodiment is illustrated in FIG. 30 whereby the system is reconfigured for dispensing. The dispense manifold 136 is installed and secured, such as by welding or aseptic connector. The median (e.g. bar code) associated with the manifold is interrogated, uploading parameter information in accordance with this disclosure. Uploading can also include manifold characteristics. Priming for filling is illustrated in FIG. 31 wherein a prime sequence is initiated which automatically stops based on gravimetric feedback and predetermined manifold hold-up. For example, the operator or a recipe or control logic sets the number of containers 137 to be filled and aliquot quantity. With the prime sequence initiated, the sequence automatically stops based on gravimetric feedback and predetermined manifold hold up. Valves V8 through V19 open or close access to its associated container 137. Typically containers 137 are filled one at a time until the programmed or selected weight or volume is attained consistent with the volume of each container and the make-up of the product bioprocessing fluid. One or more or all of the containers 137 can be filled with purified, filtered and/or collected product The process continues as illustrated in FIG. 32 automatically filling the desired number of containers 137 to a programmed set point. Filling proceeds until the program is completed. When desired, labels are printed as the containers are filled, so as to be in compliance with URS addendum requirements. Complete recovery is shown in FIG. 33, with the system typically being designed to capture as much hold-up volume as possible. If any fluid is in a container stem or the like, filtered air is provided to push as yet unrecovered fluid into the quality control container 138. For example, air via gas flow meter 135 flows through open valves 134c, 134b and V19 for access to the quality control container 138 or other container as desired. The quality control container 138 is sized based on available options and step hold-up volume. One can consider that the amount in the quality control container equals the line volume.

Figure 34:
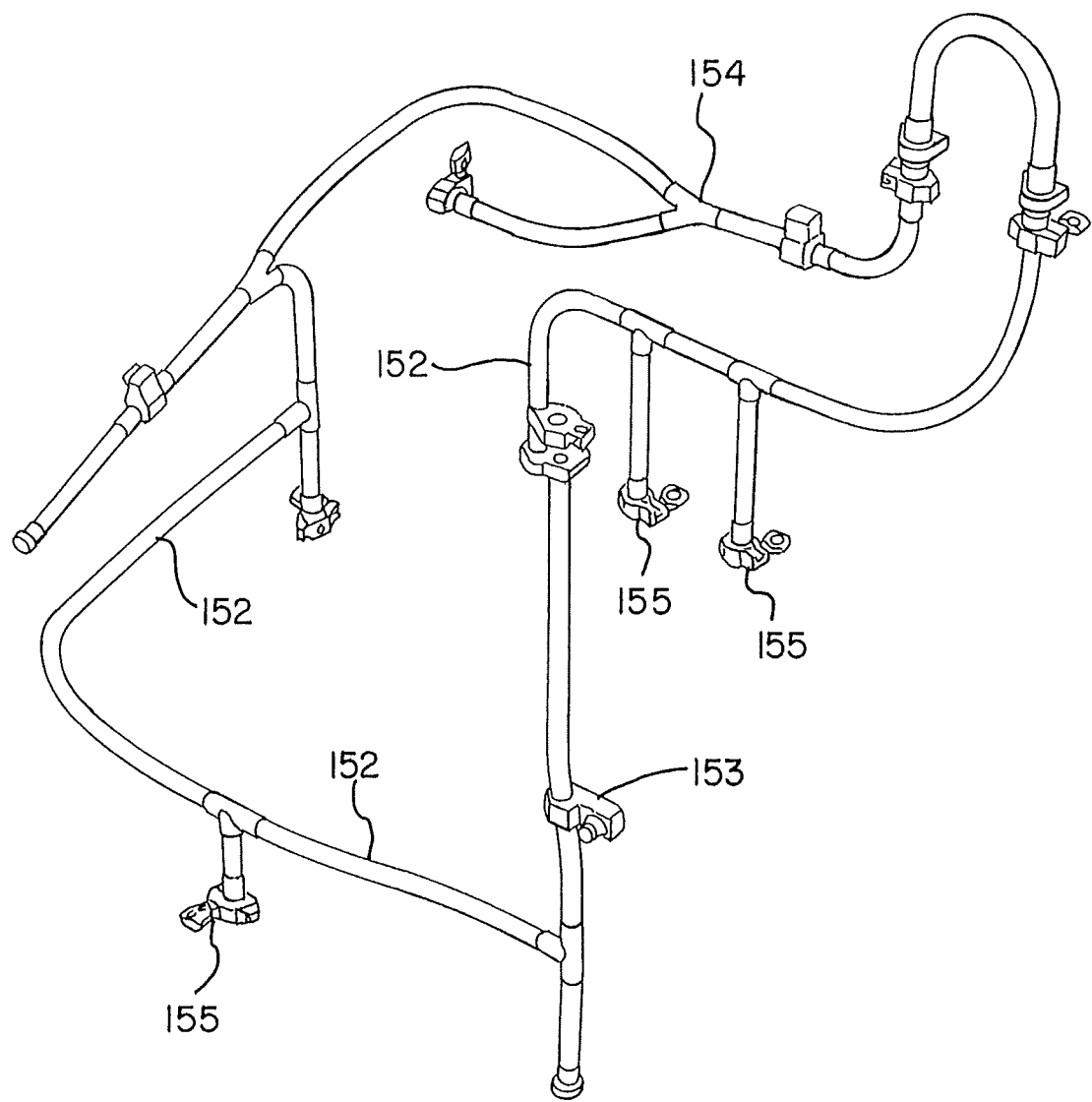
FIG. 34 is a perspective view of an embodiment of a manifold arrangement having modular capabilities.

The embodiment of manifold, generally designated at 151 in FIG. 34, illustrates the modular nature of manifolds of this disclosure. Tubes 152, valves 153, joints 154 and connectors 155 are shown. The manifold system can be designed based on container requirements, joints or connections desired, keying, valving or other one-way installation features. The GMP traceability of manifold production can be tied into production labels. It will be appreciated that features of this type allow for flexibility and additional manifold design additions allow significant hardware modifications.

Figure 35:
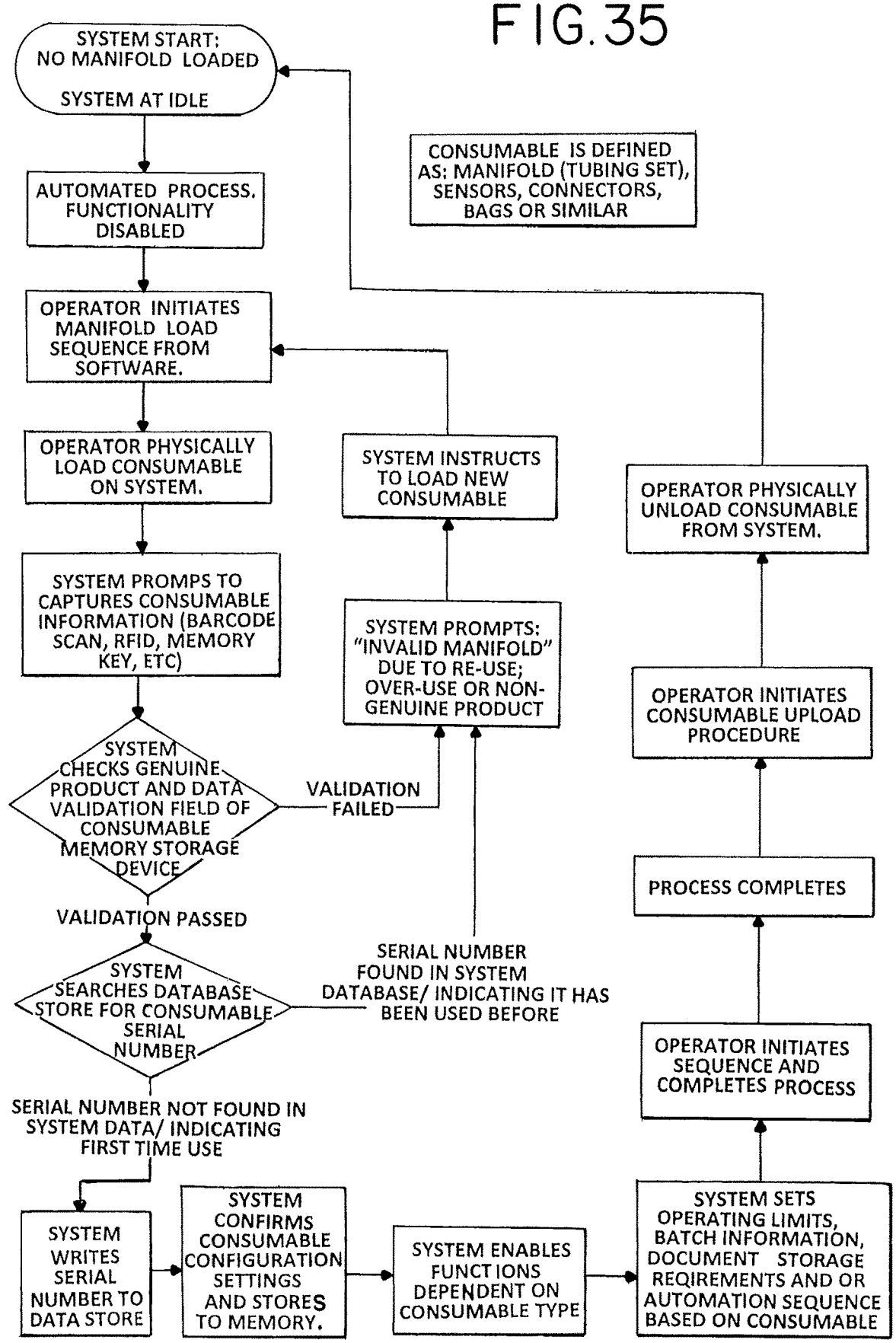
FIG. 35 is a flow chart illustrating details of an embodiment of a parameter assurance system including lock-out logic.

The flow chart of FIG. 35 illustrates details of multiple stages of an overall embodiment or embodiments. The full flow chart illustrates various options that can be included or excluded as desired. With the system initiated, the operator loads a consumable or a plurality of consumables, and the system prompts to capture consumable information by any of a variety of information storage and retrieval approaches. These include one or more of the medians for pulling and transmitting information discussed herein, such as bar code, RFID, hard wiring, wireless, memory key and the like such as those noted elsewhere herein. This allows for the operating logic that controls interrogation of the specific consumable with respect to one or more of each of its readable tolerance specifications defining suitability of the consumable for use in the particular system. If the validation fails, messaging and/or interlocking or stoppage ensues until a new consumable is loaded. Typically the operational logic determines whether or not the specific consumable is operating consistent with the readable tolerance specification for the consumable and/or for the non-consumable, system or method.

If the validation interrogation passes, in the illustrated embodiment of FIG. 35, the system searches for consumable serial numbers. If located, this indicates the serial number is in the system and thus the consumable has been previously used, leading to messaging and/or interlocking similar to the validation failed path. If a serial number is not found in the system, this indicates a first-time use; appropriate information is located, stored and/or generated as needed.

In the FIG. 35 illustrated embodiment, the system sets operating limits, batch information, document storage requirements and/or an automation sequence, typically primarily based upon the recognition of the information from that particular consumable. Once the process is completed, this embodiment requires the operator to physically unload the consumable before proceeding with a subsequent operation.

Figure 36:
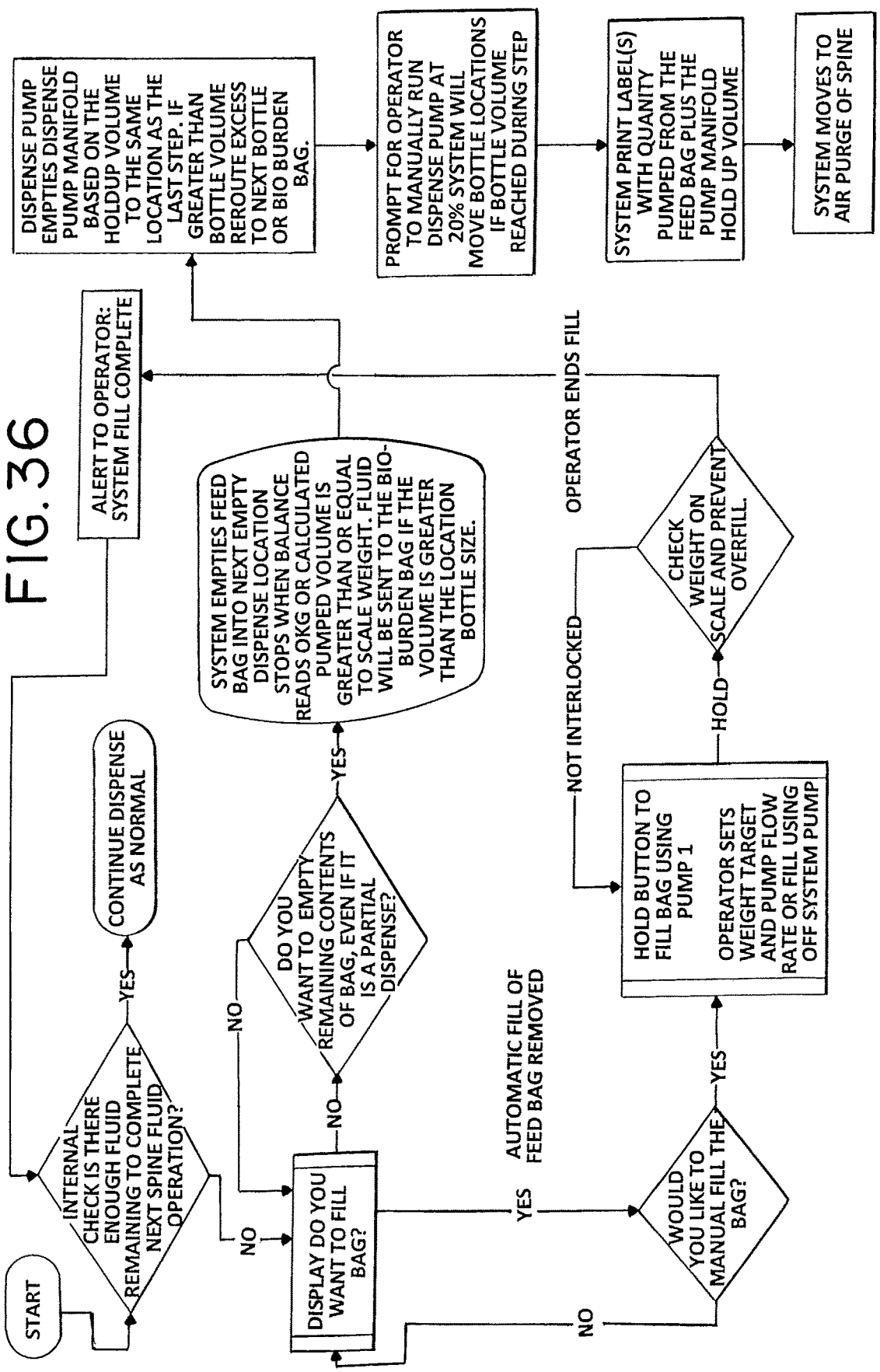
FIG. 36 is a flow chart illustrating details of a filtration and dispense system top-up module for filling bioprocessing fluid into the system.

FIG. 36 is a flow chart illustrating operational or software architecture details for an embodiment of a top-up module operation of the system and method. This functions to fill an intermediate quantification container with product to be dispensed for filtration or other operation such as discussed herein. In an embodiment, product is filled according to volume specified by the automated system. In another embodiment, a dispense sample size parameter is included in the dispense Spine setup screen for the system and method allows the user to set the quantity of the fluid dispensed during a sample for dispense Spines, typically those considered to be of a standard recipe. This enforces the minimum and maximum sample dispense amounts equal to the same limits as the other bottles of the Spine. Otherwise, in a fallback mode the dispensed sample amount is equal to that of the other containers, bottles or bags of the Spine. Typical maximum fill amounts for a container can be set to a value less than 100% of the container volume. Maximum amounts of 80% or 85% are examples, found to positively affect fluid movement in the system.

When the user chooses to top-up, an embodiment of the system and method present the user with a prompt to enter both a target weight and a feed pump flow rate. With this embodiment, the user is required to enter a maximum fill time (in minutes). After implementing the "run" mode, the system will pump until the first of three criteria is met, namely: the stop button is pressed, the fill time set at the timer expires, or the target weight is reached.

The flow charts of FIG. 36 through FIG. 40 at times reference a Spine fluid operation. The Spine is the flow path that connects the intermediate holding container with the fluid containers that are to be filled. The term Spine Fluid refers to the biotechnology fluid that is to be filled by the user of the system, such as biopharmaceutical fluids, preparation buffers, media buffers, water used in making buffers, developmental drug products, clinical drug products, commercial drug products, organic solutions and other organic materials, and others as discussed elsewhere herein. The Spine Mode is the dispensing module where fluid flows through the designated flow path into containers or other collectors.

Figure 37:
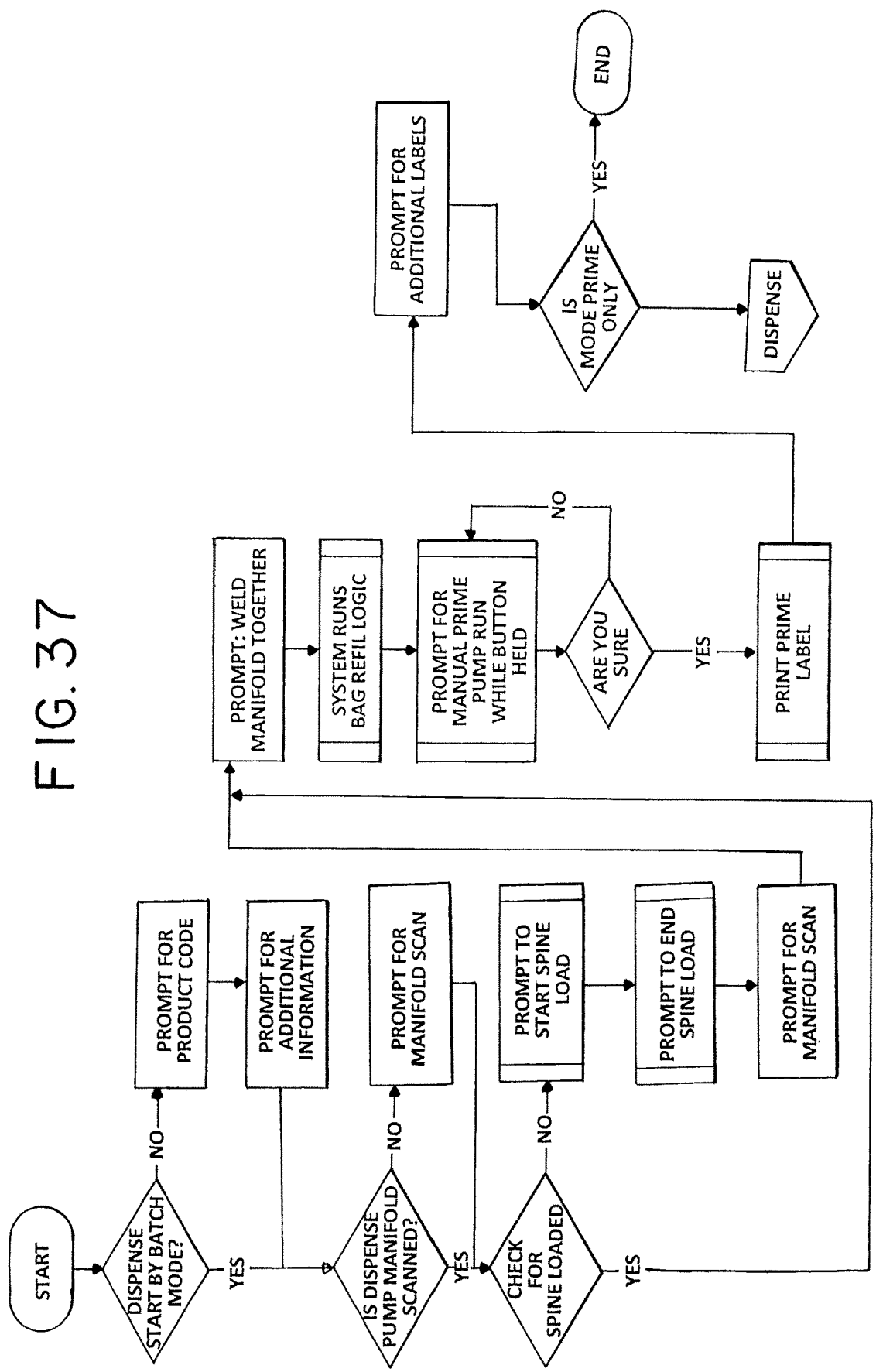
FIG. 37 is a flow chart illustrating details of a filtration and dispense system prime module for filling prior to dispensing.

FIG. 37 is a flow chart illustrating operational or software architecture details for an embodiment of a prime module operation of the system and method. This prime module functions to fill the system, such as manifold tubing and other components, with product prior to the dispense unit operation. Filling the Spine with product purges air from the line and increases the accuracy of each dispense. Priming of the line in this embodiment is automated with required parameters programmed into the system. An embodiment of a dispense prime mode has an operator initiate prime via a single method execution or a batch execution. The system can scan to make sure manifold or other consumable information is stored in the system. If this gives a failed message the display can prompt for bar code scanning (or other medium application) or manual entry of manifold and/or components information. If the manifold is not loaded, a prompt can be displayed. After load sequence is followed, all valves are open on dispensing manifold. Once the manifold is loaded and confirmed, all valves close on the dispensing manifold. A display can appear to prompt medium application (e.g. bar code scanning), and data is saved in memory. With an abort option, if followed, closes on dispensing manifold close. If no abort or alarm mode, dispense prime completes and is so signaled.

In an embodiment, before the prime sequence of the dispense method is run; the system will check and prompt the user if a fill of the container, bottle or bag is required. This will occur before every prime when this embodiment is practiced. For example, the system will prompt the user inquiring "does the feed bag need to be filled? The system state prior to this action taking place will impact on the need for user intervention.

During a dispense mode, after the system has run a top-up cycle, an embodiment provides an onscreen prompt stating that the top-up cycle has completed and the system will resume the next phase of operation. In a specific example, the system will prompt the user: "Do you want to return to top-up or continue to dispense?

In one embodiment, if the user presses "yes" to an inquiry: "Is the pump primed?", the dispense Spine will be primed automatically. In another embodiment, the user is not prompted whether or not the system is primed. Instead, prior to priming action taking place, the user is always presented with a manual prime dialog box where the user can adjust the prime as needed.

FIG. 38 is a flow chart illustrating operational or software architecture details for an embodiment of a dispense module operation of the system and method. In the dispense mode, information from the flow path is used to dispense processed product for collection such as into storage containers. The system is able to dispense product according to the container volume indicated by the flow path. Dispensing occurs from the intermediate storage container according to this embodiment thereby quantifying the amount of processed product to be dispensed.

In a dispense module embodiment, a prompt checks for scanned in memory. A prompt can be received to input the number of containers to be filled on the manifold. A prompt can be received to input the amount of fluid to be dispensed. If less than 80% (or other value such as 85%) of container volume, the system continues; if equal to or greater than 80% (or other percentage) of container volume, system does not proceed and a prompt is received that the value is too high and to make a change. Flow rate entry checked for adequacy by system, and if too high returns to value input. Similar prompts and checks can be included for stored parameters, welding of static manifold and dispense manifold together, checking pump head position. The method loads the stored parameters and initiates sequence. Further the system can ensure the valve to the filter vent is closed and the valve to the first container or bag is open. The pump executes at the programmed rate. The system can check for accurately filled container or bag, the pump stops and the valve is closed. Labels can be then printed. The display can indicate all containers are filled or not and containers can be sealed.

FIG. 39 is a flow chart illustrating operational or software architecture details for an embodiment of a sample module operation of the system and method. This module functions as a method to dispense some product for sampling purposes. This can be a component of quality control. In an embodiment features of the dispense module proceed, except a sample volume is chosen.

FIG. 40 is a flow chart illustrating operational or software architecture details for an embodiment of a chase module operation of the system and method. This module functions to clear the filling lines of remaining product and capture remaining liquid or other fluid to prevent waste of processed product.

The various modules of FIG. 36 through FIG. 40 are linked together by the fluid flow path. The filling system software encompasses all of the modules for controlling operation and interaction sequencing of the modules. It will be appreciated that specific objectives and requirements of the processing, filtration and dispensing of the biotechnical fluid will require different components and different arrangements of the components for each given use.

Certain features of some embodiments provide an especially intuitive operation in final product recovery and if refill is to proceed. If a user responds in the negative in response to a "do you want a refill" inquiry, a message will display "System will dispense reserve fluid and you will be unable to refill at this point. Do you want to continue? If no is chosen, the refill prompt returns. If yes is chosen, the control logic of the controller calculates by dividing the sensed remaining weight by the dispense setpoint. If this calculation is >1.0, then the system dispenses one additional container, bottle or bag into the next available container. Simultaneously the label will be printed reporting weight in container. The system will prompt for additional fill and labels. After the same type of calculation, the process repeats until a value<=1.0 is calculated. At this point, all of the pump volume remaining in the dispensing container (typically minus an offset to account for container weight, or example weight criteria are used in determining volume) is filled into the next container, bottle or bag, with the calculated weight being printed on the label. In an embodiment, thereafter the system and method will automatically pump the line dry into a container, bottle or bag not intended to be product. Either automatically or in response to a user prompt the system can move to bioburden "purge" to start the air purge logic.

Generally the system and method can provide a sequence of events that can be considered to fall under the general categories of: filtration sequences, dispensing sequences, method execution, loading of manifolds, and unloading of manifolds.

It will be understood that the embodiments described above are illustrative of some of the applications of the principles of the present subject matter. Automated parameter assurance systems and methods for systems and methods within which consumables and non-consumables interact and function that are constructed in accordance with this disclosure may include a number of structural and functional aspects depending on the specific design chosen. Numerous modifications may be made, including those combinations or features that are individually disclosed or claimed herein. For these reasons, the scope hereof is not limited to the above description but is set forth in the following claims, and it is understood that the claims may be directed to the features hereof, including as combinations of features that are individually disclosed or claimed herein.

The invention claimed is:

1. A system for processing bioprocessing fluids, comprising:
    a. the system includes a manifold, one or more consumables and at least one non-consumable, each consumable and non-consumable having a predetermined function, wherein the system combines the consumables and the non-consumables, the system being for bioprocessing of a bioprocessing fluid;
    b. at least one of the consumables is a specific consumable characterized by having at least one readable tolerance specification embedded within the specific consumable or within packaging for the specific consumable and the readable tolerance specification defines whether the specific consumable is configured for use in the system, wherein the readable tolerance specification is an operation detail or a parameter specification of the specific consumable, or a combination thereof;
    c. the non-consumable includes operating logic that controls interrogation of the specific consumable with respect to the readable tolerance specification thereby determining whether the specific consumable is operating consistent with the readable tolerance specification;
    d. an interlock that activates a signal to inform of non-compliance of the specific consumable when the operating logic detects operation inconsistent with the readable tolerance specification, and wherein the interlock activates a stoppage function with respect to the manifold, so as to avoid out-of-compliance operation;
    e. wherein the specific consumable includes a multipoint readable tolerance specification that is accessible by the non-consumable and operated on by the operating logic of the non-consumable; and
    f. wherein the multipoint readable tolerance specification provides redundant points, and multiple points to be read by multiple means of reading or multiple different types of reading means, wherein reads of the multipoint readable tolerance specification indicates correct location of a component within the system and minimizes possible installing of an incorrect consumable for the system or at an incorrect location within the system.

2. The system in accordance with claim 1, wherein the readable tolerance specification is selected from the group consisting of an operational detail, a parameter specification, and combinations thereof.

3. The system in accordance with claim 1, wherein the system is a manifold system, and the specific consumable is recognized as non-genuine in that the specific consumable does not meet a specific requirement of a manufacturer for use in the manifold system when the readable tolerance specification is interrogated and determined inconsistent with the readable tolerance specification.

4. The system in accordance with claim 1, wherein the operating logic is configured to probe whether or not the specific consumable is configured for use in the system and is within operational limits and parameters of the specific consumable for the system.

5. The system in accordance with claim 1, wherein the interrogation of the readable tolerance specification includes communication with the specific consumable by barcode, RFID, wireless, memory key, hard wiring, chip, engraving, label or combinations thereof.

6. The system in accordance with claim 1, wherein the bioprocessing fluid of the selected type is selected from the group consisting of biopharmaceutical fluids; preparation and media buffers; water used in making buffers; developmental, clinical and commercial drug products, components and formulations; organic solutions and other organic materials, including cells, tissue, byproduct of cell growth; adjuvants; active pharmaceutical ingredients (API's); antibodies; antibody drug conjugates; vaccines; and combinations thereof.

7. The system in accordance with claim 1, wherein the system is a fluid management system configured to perform a process selected from the group consisting of Normal Flow Filtration, Tangential Flow Filtration, Chromatography, Buffer Preparation, Media Preparation, Dispensing, Transfer Applications, Bioreactors and Fermenters.

8. The system in accordance with claim 1, wherein said specific consumable has a predetermined function within the system, the system is configured to perform a process selected from the group consisting of Normal Flow Filtration, Tangential Flow Filtration, chromatography, preparative chromatography, bioreactor applications, media preparation, media dispensing, buffer preparation, buffer dispensing, cell banking, drug or biologic fluid bottling or bagging from bulk containers or other sources, vial filling, blow molding and sealing with drug dispensing, liophilization, biologics flash freeze, cold freeze, cryogenic freeze and combinations thereof.

9. A method for processing bioprocessing fluids, comprising:
    a. providing consumables and non-consumables each having a predetermined function, wherein the consumables and non-consumables combine into a system for processing of a bioprocessing fluid of a selected type;
    b. wherein at least one of the consumables is a specific consumable characterized by at least one readable tolerance specification that defines whether the specific consumable is configured for use in the system, wherein the readable tolerance specification is an operational detail, a parameter specification, or combination thereof;

c. supplying operating logic that controls interrogating of the specific consumable with respect to said readable tolerance specification which is embedded within the specific consumable or its packaging thereby determining whether the specific consumable is operating consistent with the readable tolerance specification;

d. activating an interlock signal to inform on non-compliance of the consumable when the operating logic detects operation inconsistent with the readable tolerance specification;

e. providing a multipoint storage feature for the specific consumable; and f. wherein the multipoint storage feature provides redundant points, and multiple points to be read by multiple means of reading or multiple different types of reading means, wherein reading of the multipoint readable tolerance specification indicates correct location of a component within the system and minimizes possible installing of an incorrect consumable for the system or at an incorrect location within the system.

10. The method in accordance with claim 9, wherein the readable tolerance specification is selected from the group consisting of an operational detail, a parameter specification, and combinations thereof.

11. The method in accordance with claim 9, wherein the system includes a manifold, and the interrogating of the specific consumable is recognized as non-genuine in that the specific consumable does not meet a specific requirement of a manufacturer for use in the manifold system when the readable tolerance specification is determined, after such interrogating, to be inconsistent with the readable tolerance specification.

12. The method in accordance with claim 9, wherein the operating logic is configured to probe whether or not the specific consumable is installed and is within the operational limits and parameters of the specific consumable for said method within which the specific consumable is to be used or with which it the specific consumable is to be interfaced.

13. The method in accordance with claim 9, further including providing communication with the specific consumable for interrogation of the readable tolerance specification by barcode, RFID, wireless, memory key, hard wiring, chip, engraving, label or combinations thereof.

14. The method in accordance with claim 9, wherein the system includes a manifold, and the signal activating includes interlocking that activates a stoppage function with respect to the manifold system capable of avoiding out-of-compliance operation.

15. The method in accordance with claim 9, wherein the bioprocessing fluid of the selected type is selected from the group consisting of biopharmaceutical fluids; preparation and media buffers; water used in making buffers; developmental, clinical and commercial drug products, components and formulations; organic solutions and other organic materials, including cells, tissue, byproduct of cell growth; adjuvants; active pharmaceutical ingredients (API's); antibodies; antibody drug conjugates; vaccines; and combinations thereof.

16. The method in accordance with claim 9, wherein the consumable has a predetermined function within the method, the method being configured to perform a process selected from the group consisting of Normal Flow Filtration, Tangential Flow Filtration, chromatography, preparative chromatography, bioreactor applications, media preparation, media dispensing, buffer preparation, buffer dispensing, cell banking, drug or biologic fluid bottling or bagging from bulk containers or other sources, vial filling, blow molding and sealing with drug dispensing, liophilization, biologics flash freeze, cold freeze, cryogenic freeze and combinations thereof.

* * * * *